US012690761B2

(12) United States Patent
    Walker

(10) Patent No.: US 12,690,761 B2
(45) Date of Patent: Jul. 28, 2026

(54) VIDEO LARYNGOSCOPIC TRACHEOSCOPE

(71) Applicant: Brandon Walker, San Antonio, TX (US)

(72) Inventor: Brandon Walker, San Antonio, TX (US)

( * ) Notice: Subject to any disclaimer, the term of this patent is extended or adjusted under 35 U.S.C. 154(b) by 0 days.

(21) Appl. No.: 18/816,770

(22) Filed: Aug. 27, 2024

(65) Prior Publication Data

US 2025/0072741 A1     Mar. 6, 2025

Related U.S. Application Data

(60) Provisional application No. 63/534,984, filed on Aug. 28, 2023.

(51) Int. Cl.
    *A61B 1/267*      (2006.01)
    *A61B 1/015*      (2006.01)
    *A61B 1/12*       (2006.01)

(52) U.S. Cl.
    CPC .............. *A61B 1/267* (2013.01); *A61B 1/015* (2013.01); *A61B 1/127* (2013.01)

(58) Field of Classification Search
    CPC ............................... A61B 1/267; A61B 1/2676
    See application file for complete search history.

(56) References Cited

U.S. PATENT DOCUMENTS

| | | | | |
|---|---|---|---|---|
| 4,905,666 | A | * | 3/1990 | Fukuda ................ A61B 1/0052 |
| | | | | 600/146 |
| 2001/0023312 | A1 | * | 9/2001 | Pacey .................... A61B 1/267 |
| | | | | 128/207.14 |
| 2013/0066151 | A1 | * | 3/2013 | Chen .................. A61B 1/00048 |
| | | | | 600/188 |
| 2014/0309494 | A1 | * | 10/2014 | Molnar ................ A61B 1/0676 |
| | | | | 600/109 |

* cited by examiner

*Primary Examiner* — Julianna N Harvey
(74) *Attorney, Agent, or Firm* — Dykema Gossett PLLC

(57)                    ABSTRACT

Apparatus and methods for placement of an endotracheal tube in an airway of a patient, where the apparatus includes a laryngoscope member with a camera and a suction aperture for clearing unwanted material from the camera, where the laryngoscope member includes a lumen for passage of a tracheoscope member that also has a camera and a suction aperture for clearing unwanted material from the camera, where an endotracheal tube can be advanced over the tracheoscope member and positioned as desired in the airway of the patient, where the cameras facilitate positioning of the laryngoscope member, tracheoscope member, and endotracheal tube, and the suction apertures facilitate clearing unwanted material that could otherwise obscure imaging by the cameras.

12 Claims, 16 Drawing Sheets

VIDEO LARYNGOSCOPIC TRACHEOSCOPE

RELATED APPLICATIONS

This application claims the benefit of U.S. Provisional Application No. 63/534,984, filed on Aug. 28, 2023, which application(s) are incorporated herein by reference in their entirety.

FIELD

Embodiments disclosed in the present disclosure relate to devices and methods for access to an airway of a patient. More specifically, embodiments disclosed herein relate to apparatus for placement of an endotracheal tube into an airway of a patient. Embodiments disclosed herein additionally relate to methods of fabrication of a laryngoscopic tracheoscope, and methods of accessing an airway of a patient using a video laryngoscopic tracheoscope.

BACKGROUND ART

Laryngoscopes are often used to facilitate placement of an endotracheal tube (ETT) into an airway of a patient to provide for effective respiration, secure access for inhalation anesthetics and other materials, provide for positive-pressure ventilation, reduce risk of ingress of gastric contents, blood, or other undesired materials into the lungs, and so forth. Laryngoscopes can include lighting to facilitate visualization, and can also include video cameras for enhanced visualization of anatomic structures to facilitate placement of an endotracheal tube or other diagnostic or therapeutic procedures. One problem associated with existing laryngoscopes is that they provide a limited range of visualization, and typically only provide adequate visualization to the level of the vocal cords in the patient. Thus, when advancing the endotracheal tube, oftentimes, the endotracheal tube can be advanced into an esophagus of the patient, which can have serious undesired consequences.

Furthermore, as a laryngoscope is advanced through a patient's larynx, a camera associated with the laryngoscope can become clouded or obscured by secretions, gastric contents, and/or blood located in the patient's larynx, interfering with visualization and making it difficult to determine exactly where the laryngoscope is placed.

Embodiments disclosed herein provide improvements that address limitations associated with the prior art.

BRIEF SUMMARY

Embodiments disclosed herein can include a laryngoscopic tracheoscope having a laryngoscope member including a first lumen for passage of a tracheoscope member within the first lumen, where an endotracheal tube can be advanced over the tracheoscope member within the first lumen, to facilitate placement of the endotracheal tube in an airway of a patient. In some embodiments, the laryngoscopic tracheoscope includes camera apparatus, light apparatus, and a suction system for clearing unwanted material which could otherwise interfere with imaging by the camera apparatus. In some embodiments, the laryngoscope member includes a laryngoscope camera, light, and a suction aperture for clearing unwanted material which could otherwise interfere with imaging by the laryngoscope camera. In some embodiments, the tracheoscope member includes a tracheoscope camera, light, and a suction aperture for clearing unwanted material which could otherwise interfere with imaging by the tracheoscope camera. In some embodiments, the laryngoscopic tracheoscope includes a graphical display configured to display images from the camera apparatus, which includes a laryngoscope camera and/or a tracheoscope camera.

Some embodiments disclosed herein can include an apparatus for accessing and viewing an airway of a patient, such as can be used to insert an endotracheal tube in an airway of a patient. Some embodiments disclosed herein include a laryngoscopic tracheoscope with camera imaging and suction to clear secretions, gastric contents, blood, or other unwanted material that could otherwise obscure camera imaging. Some embodiments disclosed herein include a laryngoscope member with a lumen for passage of a tracheoscope member and an endotracheal tube. In some embodiments, the laryngoscopic tracheoscope includes stop features to avoid unintentional advancement of the endotracheal tube. In some embodiments, the laryngoscopic tracheoscope includes a curving mechanism to bend and orient the distal portion of the tracheoscope member. In some embodiments, the laryngoscopic tracheoscope includes two separately-positionable cameras, with suction arranged proximate each of the cameras configured to clear unwanted material from obscuring the view of the respective camera. In some embodiments, the laryngoscopic tracheoscope includes a deformable cover enclosing a proximal portion of the laryngoscopic tracheoscope, that can be manipulated to position the tracheoscope member with respect to the laryngoscope member, and to position the endotracheal tube in the airway of the patient. In some embodiments, the apparatus includes at least one graphical display device to allow a physician, nurse, emergency personnel, veterinary personnel, or other user to view the camera imaging and thereby facilitate diagnostic or therapeutic procedure, such as placement of an endotracheal tube in an airway of an adult or a pediatric patient. In some embodiments, the graphical display device is incorporated into the laryngoscopic tracheoscope, a separate display connected via communication path or cable, or a combination.

Some embodiments disclosed herein include apparatus for placement of an endotracheal tube into an airway of a patient. Some embodiments disclosed herein include methods of fabrication of a laryngoscopic tracheoscope, and methods of accessing an airway of a patient using a laryngoscopic tracheoscope. Embodiments disclosed herein incorporate various combinations of the disclosed features, consistent with the disclosures herein.

These and various other advantages and features of novelty which characterize embodiments disclosed herein are pointed out with particularity in the claims annexed hereto and forming a part hereof. However, for a better understanding of the embodiments, advantages, and objects obtained by their use, reference should be made to the drawings which form a further part hereof, and to the accompanying descriptive matter, which illustrate and describe some embodiments consistent with the present disclosure.

BRIEF DESCRIPTION OF THE DRAWINGS

In the drawings, in which corresponding reference numerals and letters indicate corresponding parts of the various embodiments throughout the several views, and in which the various embodiments generally differ only in the manner described and/or shown, but otherwise include parts corresponding to the parts in the other various embodiments.

3

Figures 1, 2:
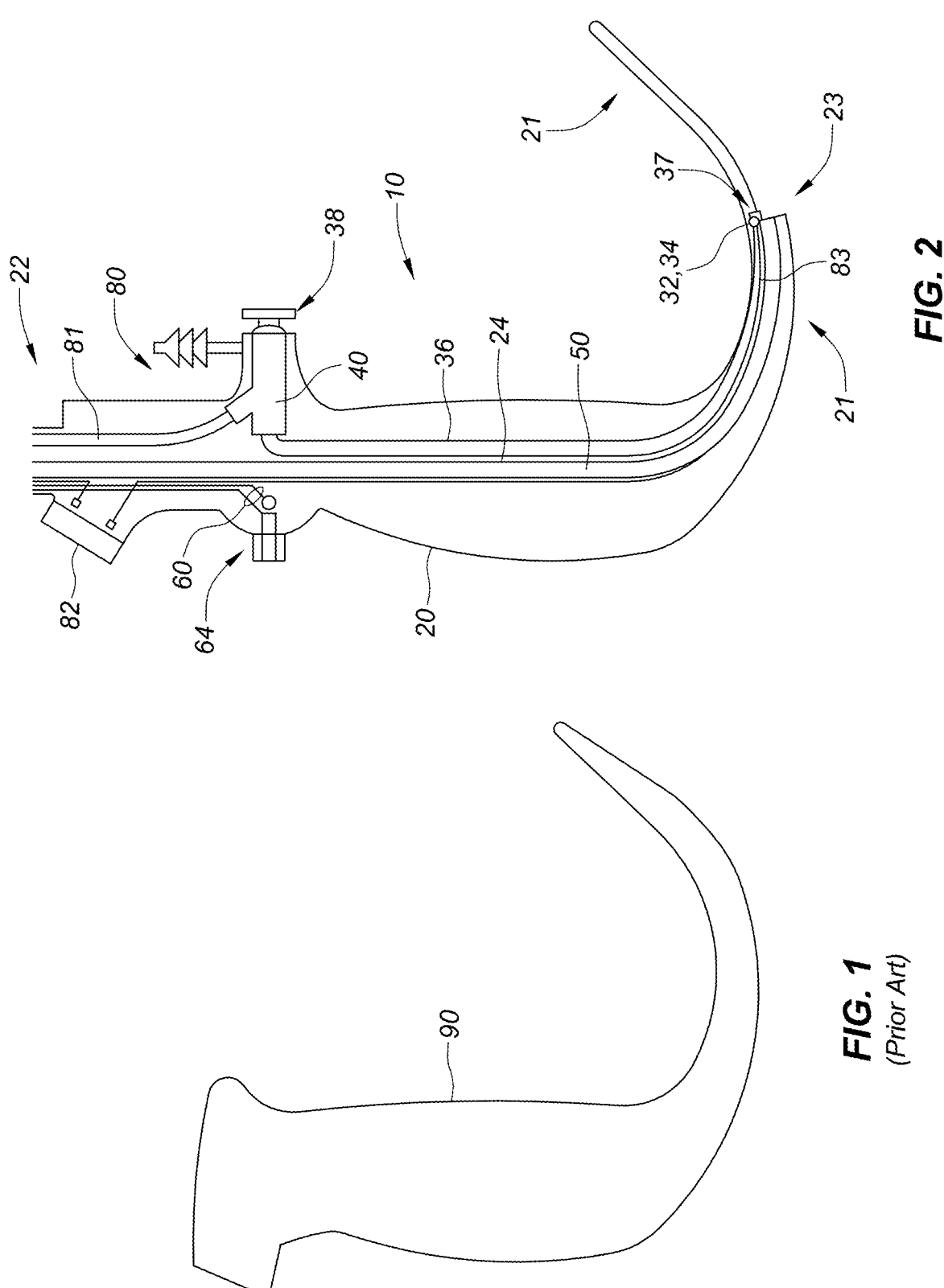
FIG. 1 is a schematic illustration of a prior art video laryngoscope.
Figure 3:
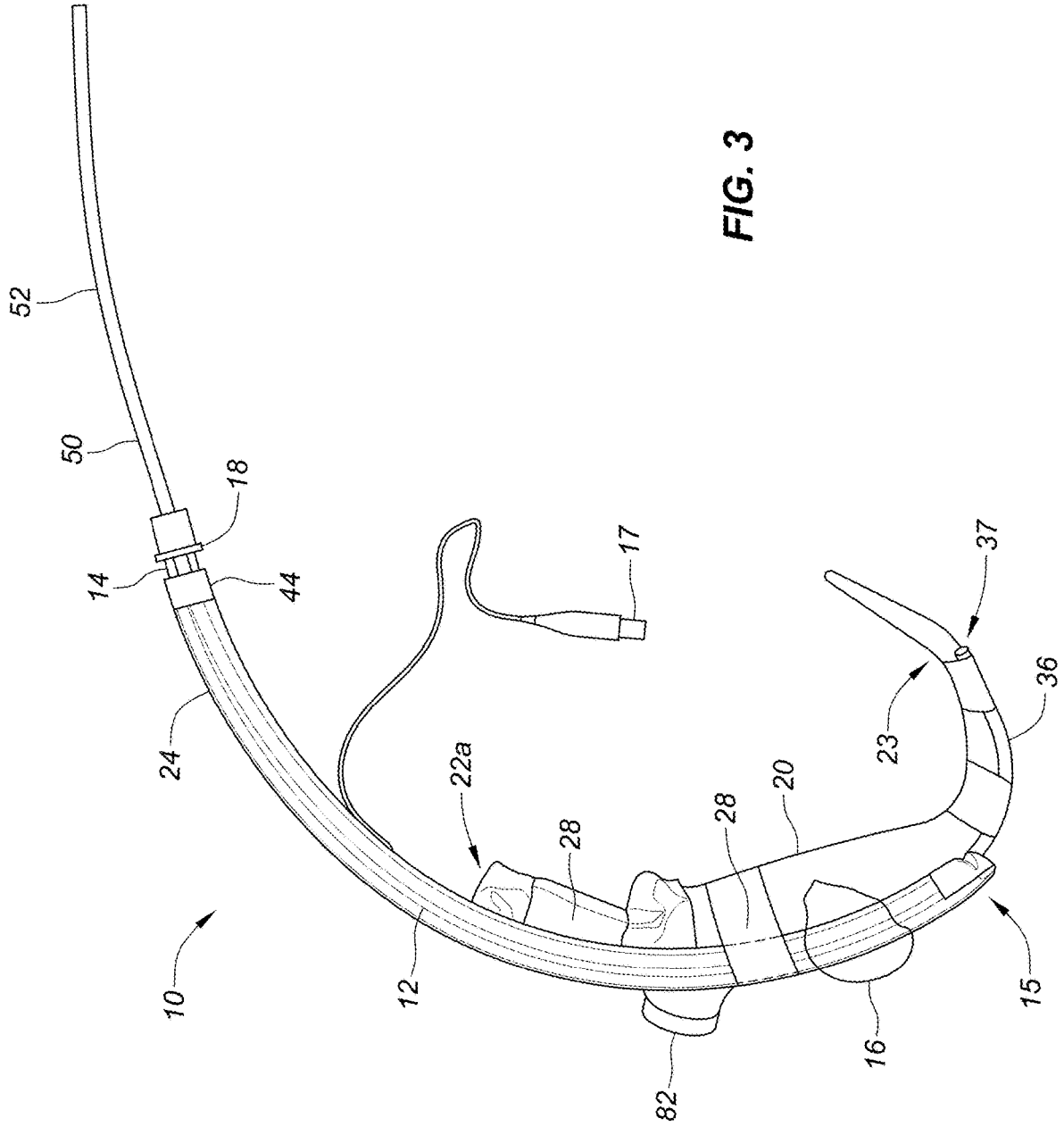
Figure 5:
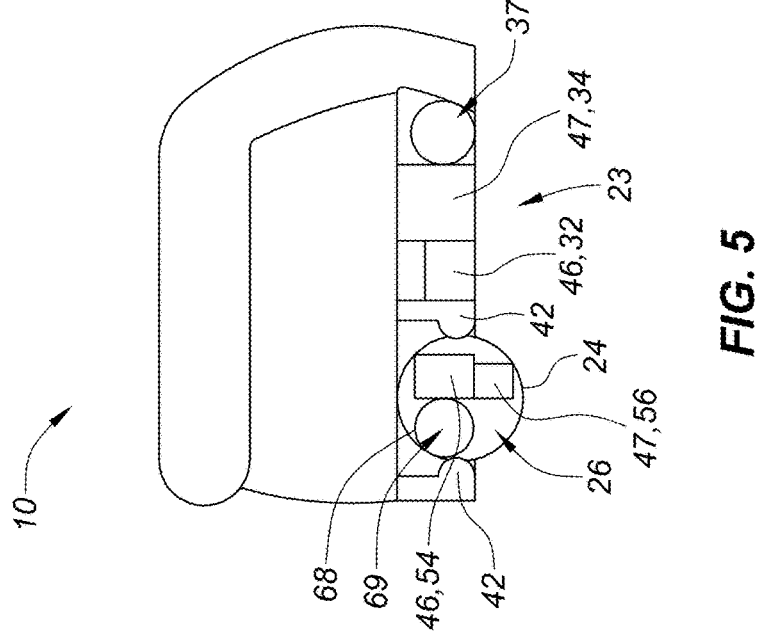
Figure 4:
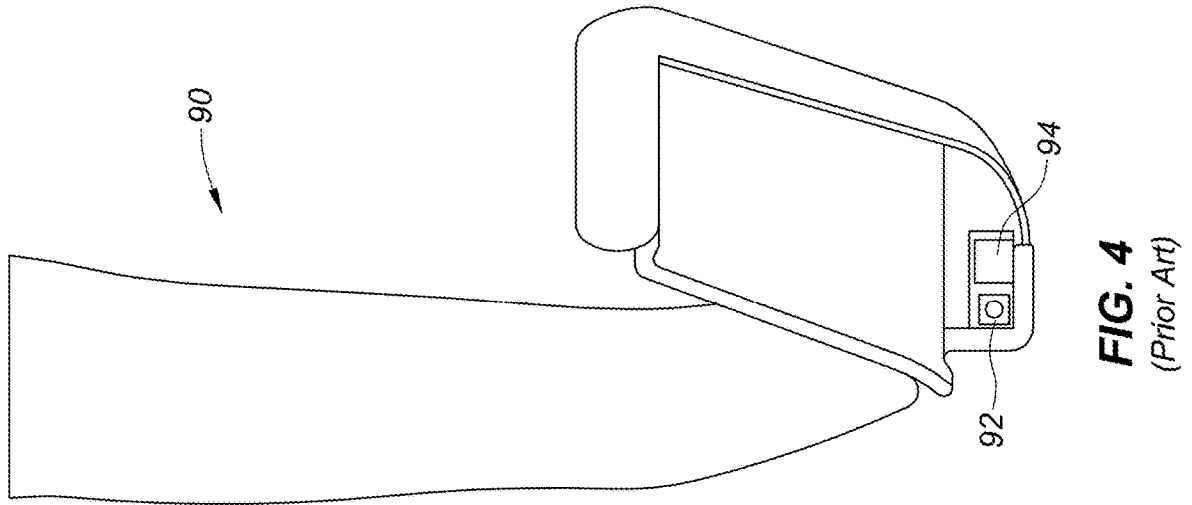
Figure 6:
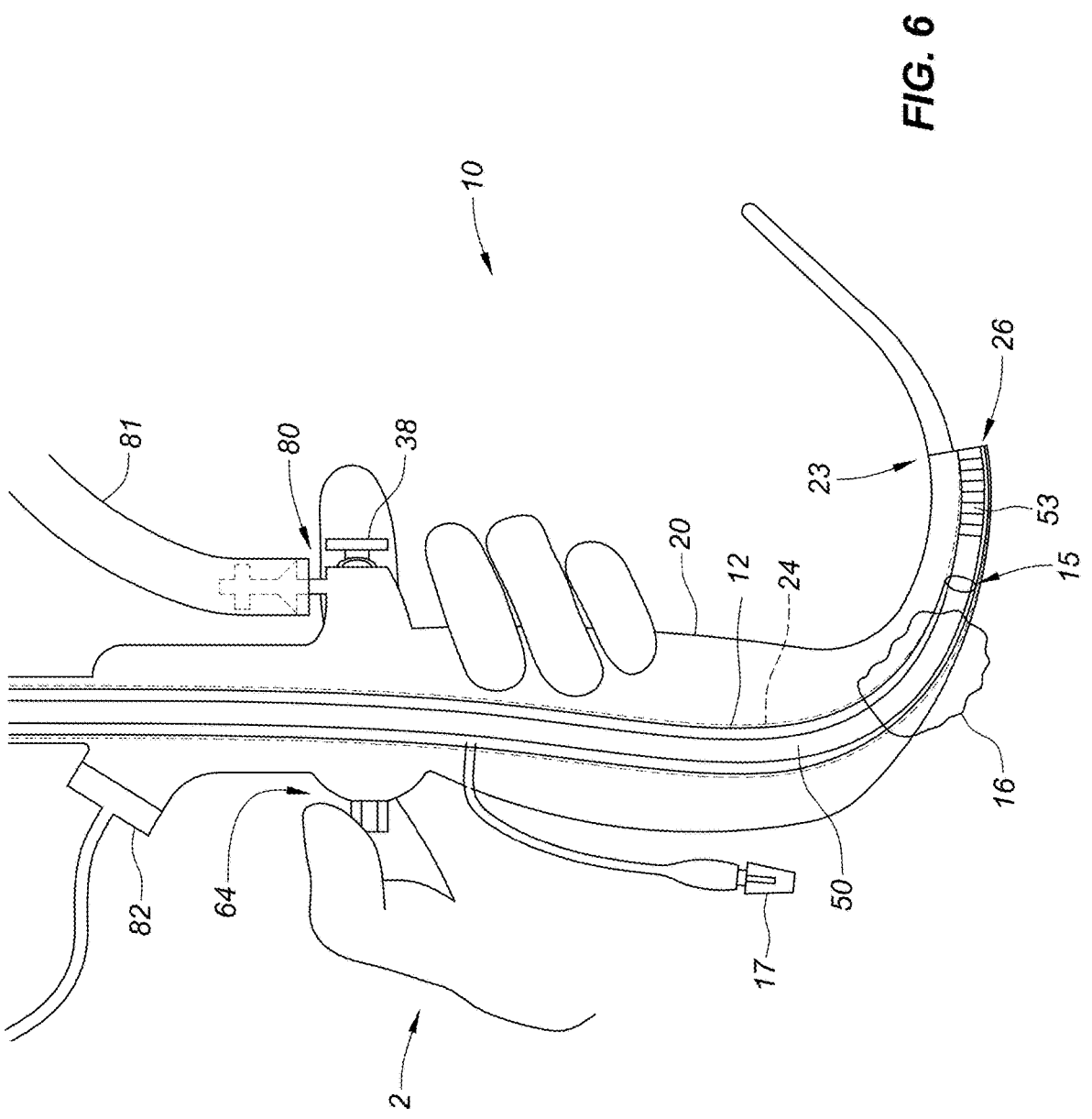
Figure 7:
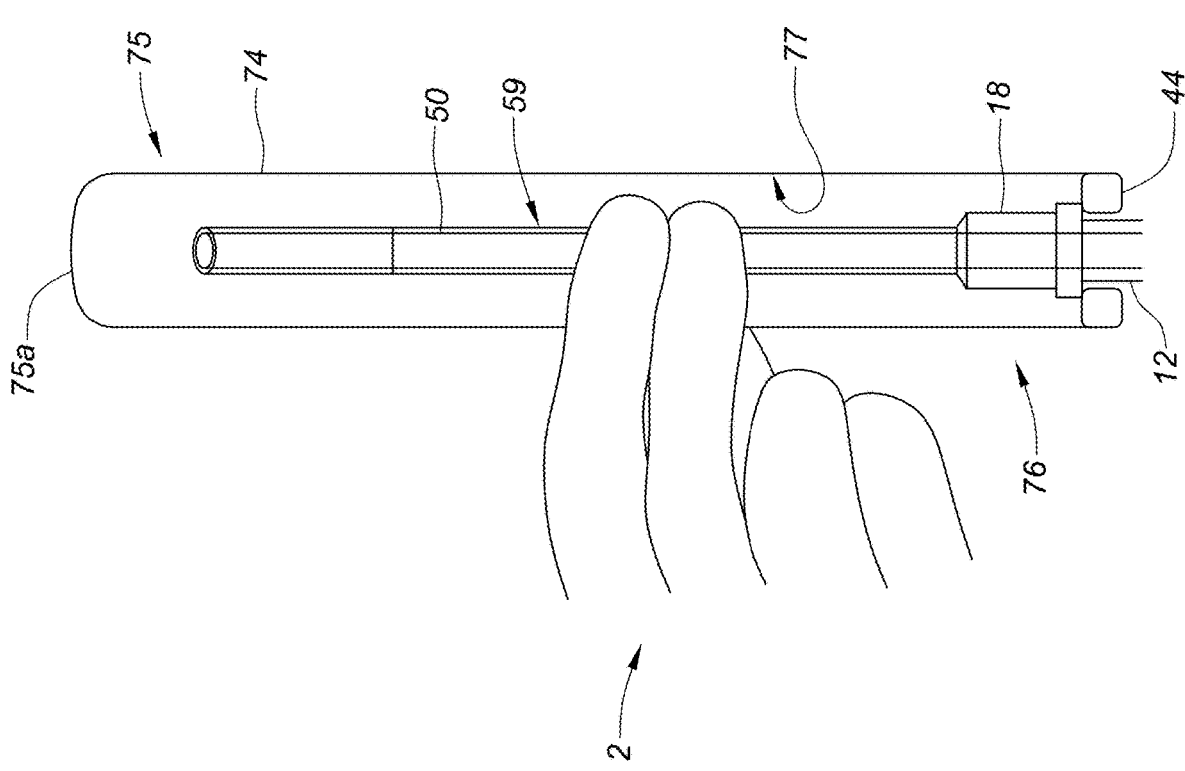
Figure 8:
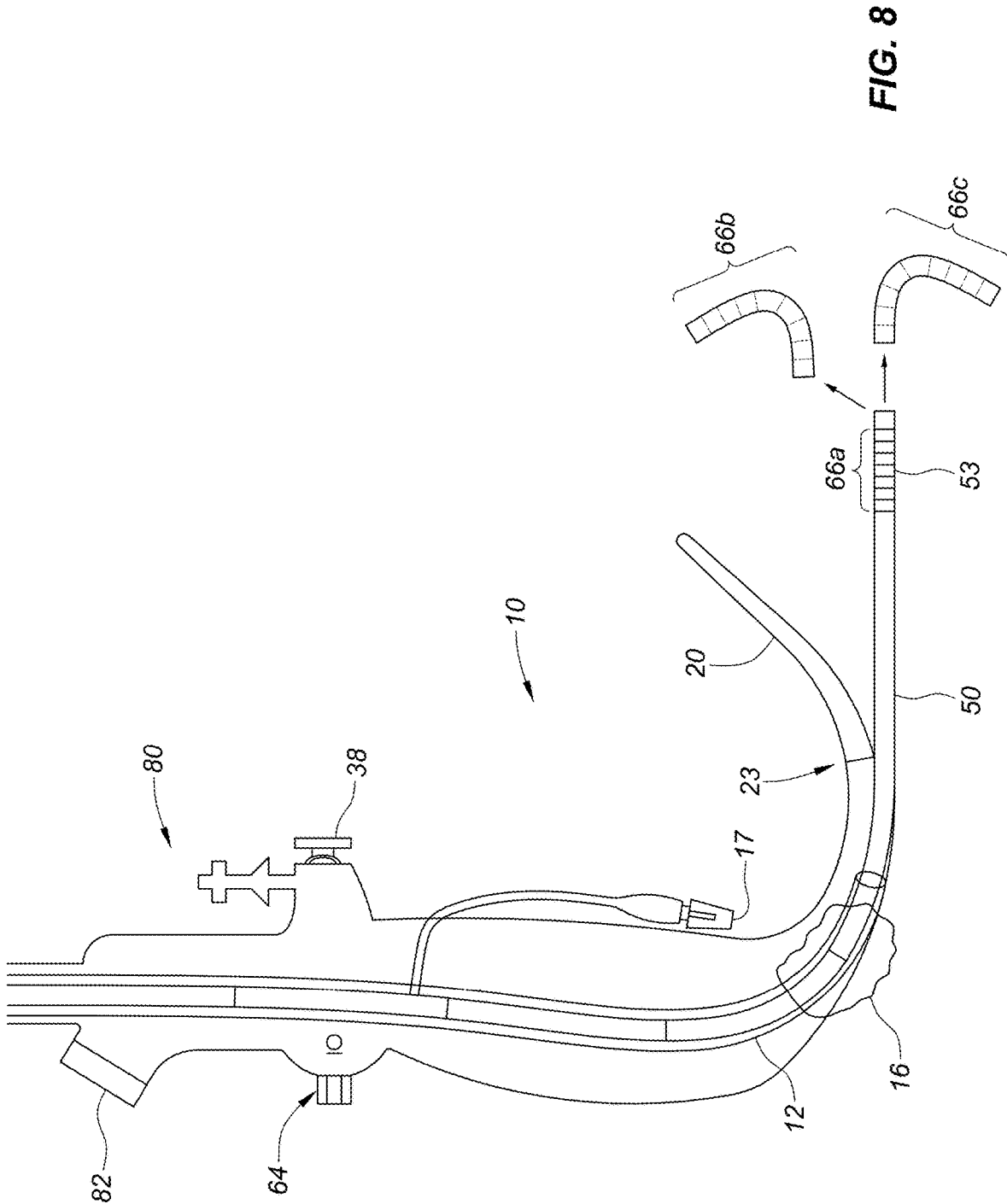
Figure 10:
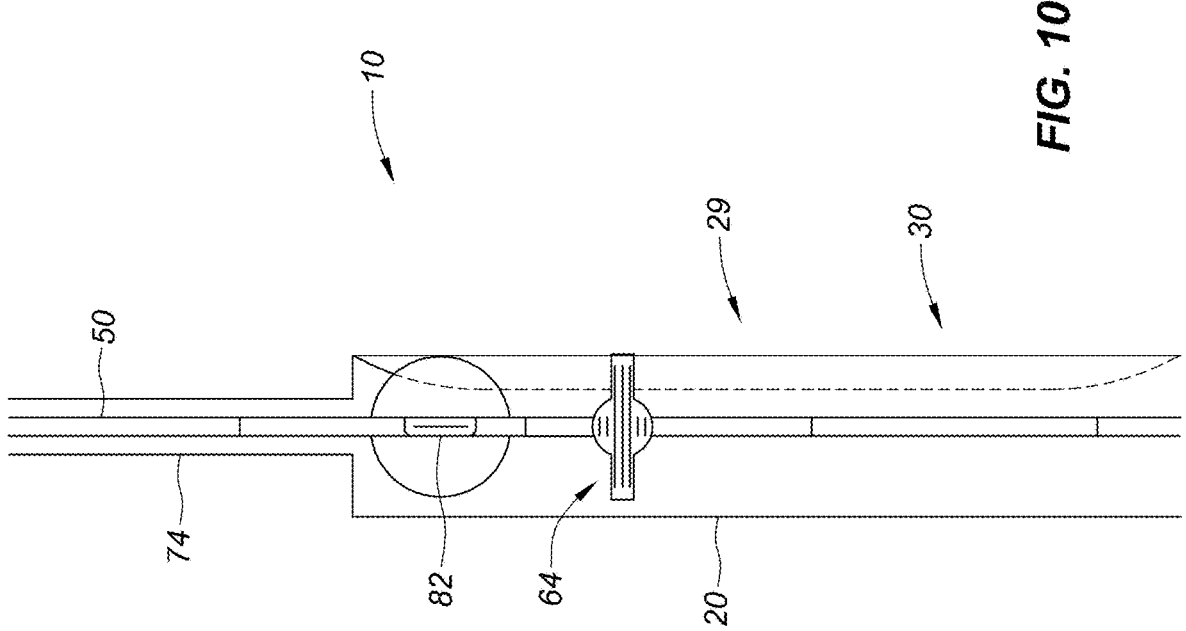
Figure 9:
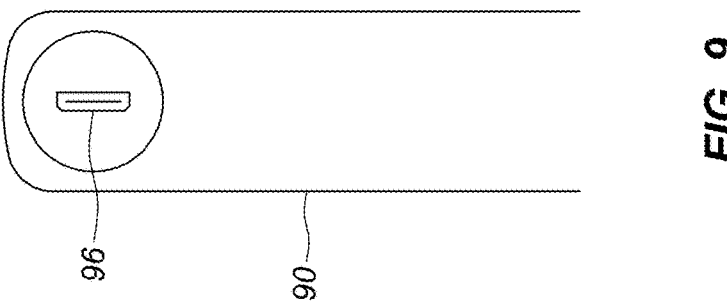
Figure 11:
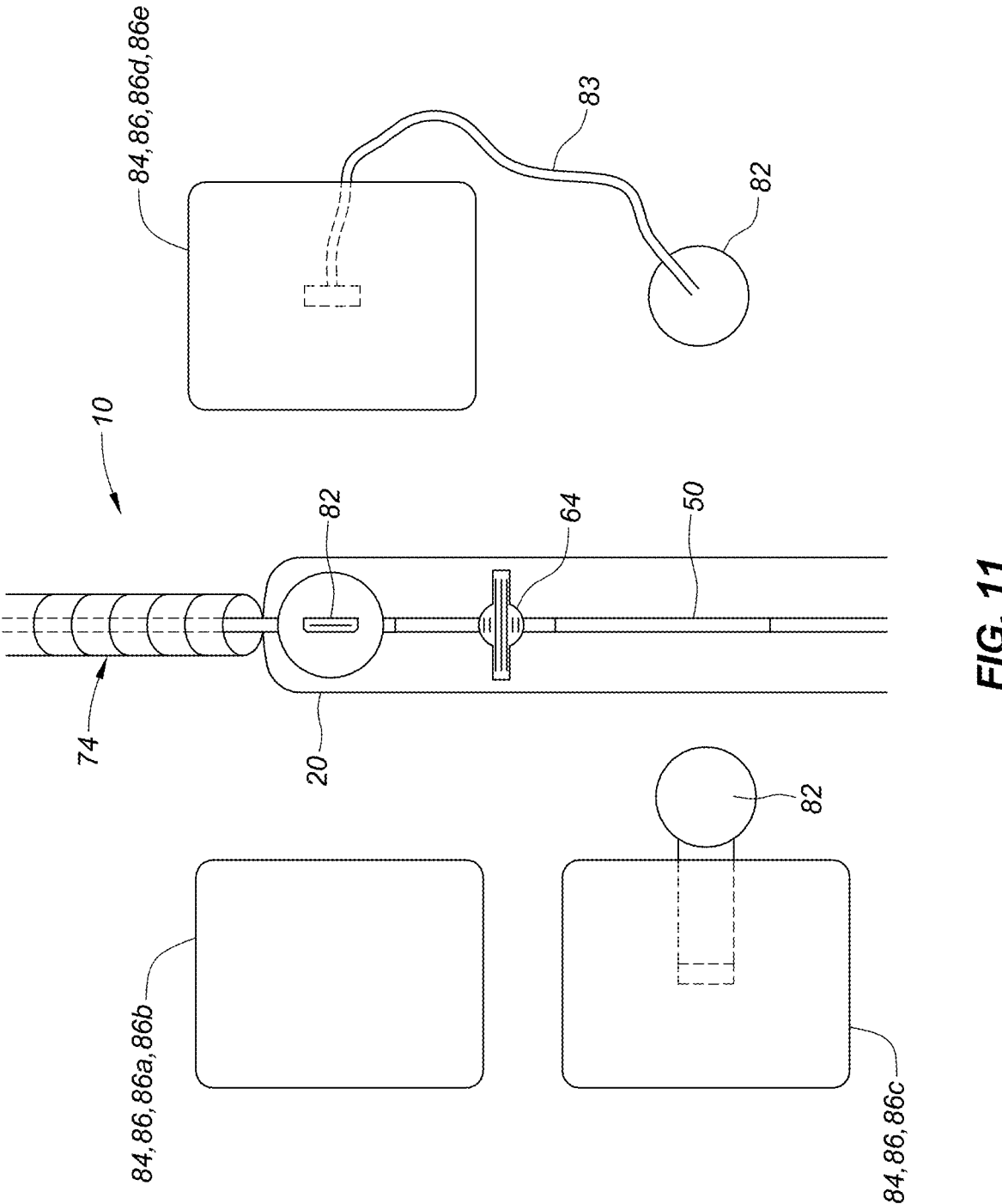
Figure 12:
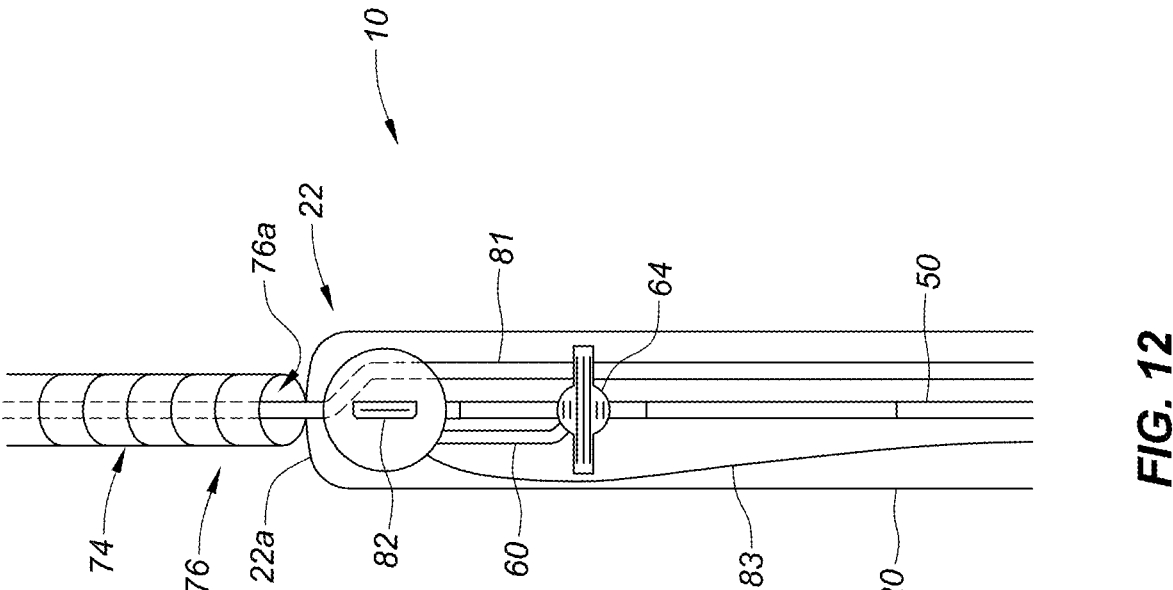
Figure 13:
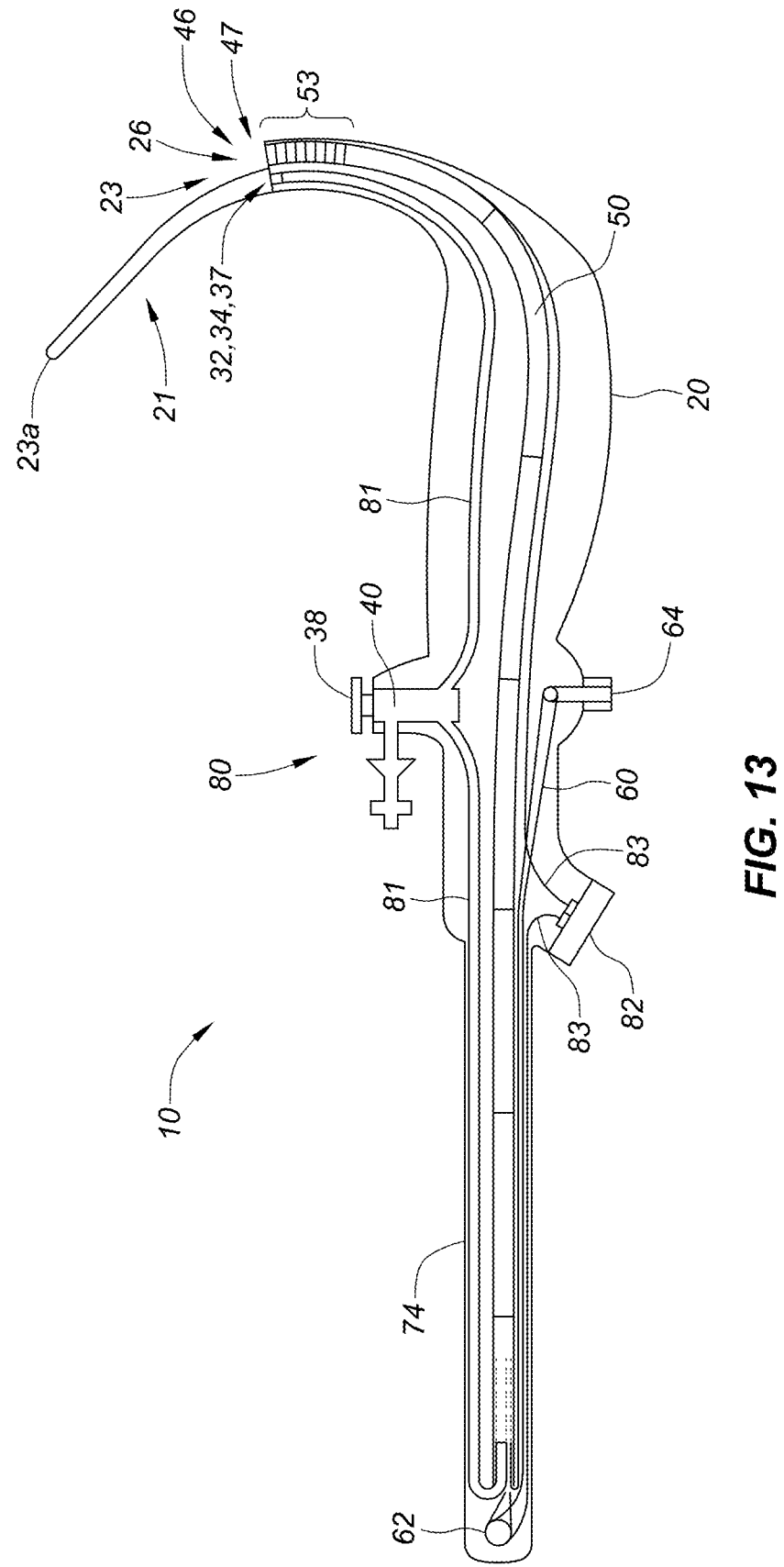
Figure 14:
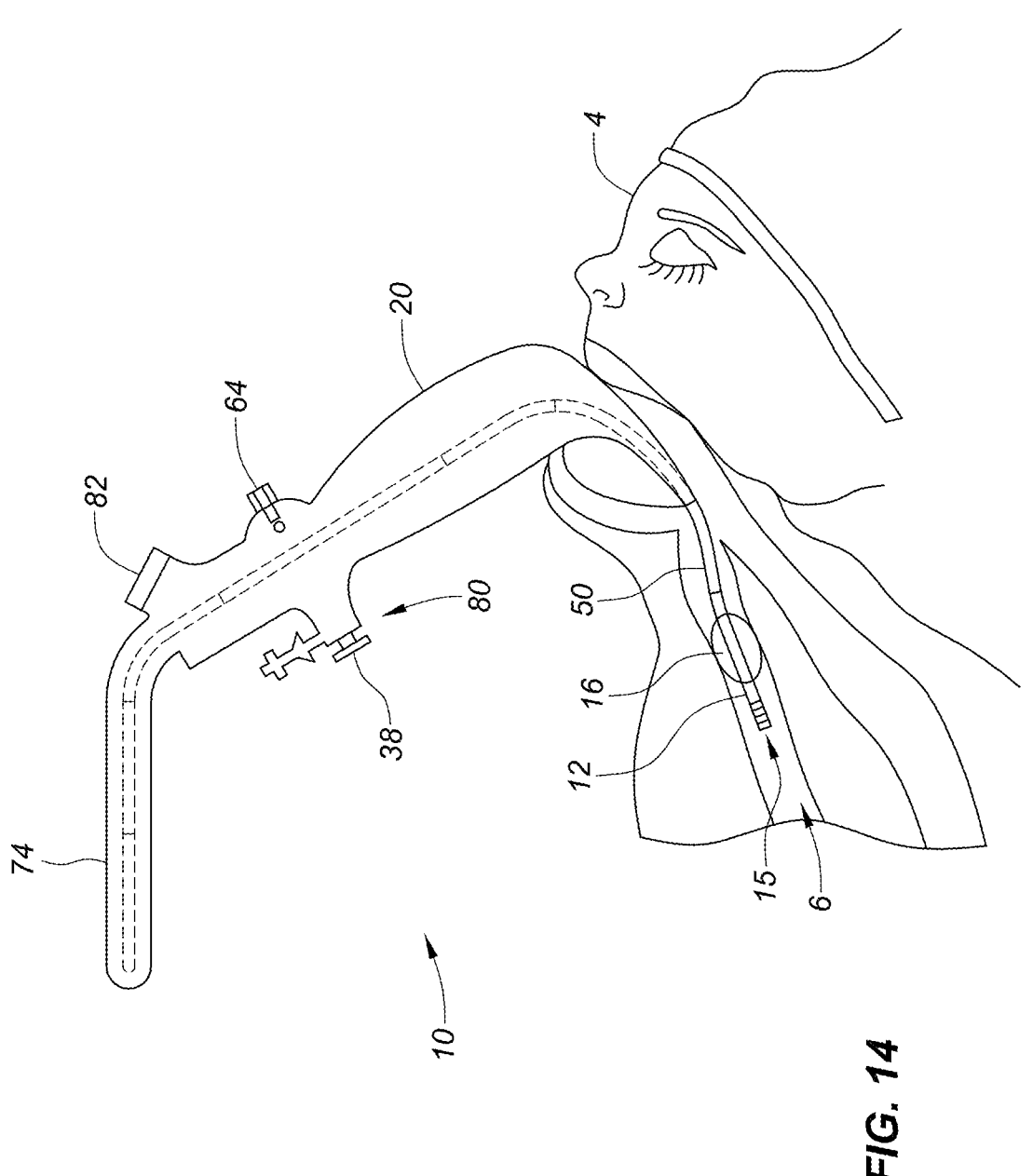

FIG. 2 is a schematic illustration of a video laryngoscopic tracheoscope in accordance with embodiments of the present disclosure, and shows a cross-sectional view of a tracheoscope member disposed within a lumen of a laryngoscope member;

FIG. 3 is a schematic side view of a video laryngoscopic tracheoscope showing a tracheoscope member disposed within lumen segments of the laryngoscope member, with an endotracheal tube arranged on the tracheoscope member;

FIG. 4 is a schematic front view of a distal portion of the prior art laryngoscope of FIG. 1;

FIG. 5 is a schematic front view of a distal portion of a laryngoscopic tracheoscope in accordance with embodiments disclosed herein, showing a tracheoscope member disposed within a lumen of a laryngoscope member, and illustrating cameras, lights, and suction apertures;

FIG. 6 is a schematic illustration showing a portion of a laryngoscopic tracheoscope in accordance with embodiments disclosed herein, showing an endotracheal tube loaded onto a tracheoscope member, disposed within a lumen of a laryngoscope member, and illustrating manual control of the apparatus, including a steering assembly for control of a curving mechanism, and a suction actuator for control of suction applied to clear unwanted material that may be present at or near a distal camera;

FIG. 7 is a schematic illustration of a proximal portion of a laryngoscopic tracheoscope in accordance with embodiments disclosed herein, with an endotracheal tube loaded onto a tracheoscope member that is loaded within a lumen of a laryngoscope member, further showing a deformable cover enclosing the proximal portion of the tracheoscope member, with the tracheoscope member being manipulated through the deformable cover;

FIG. 8 is a schematic illustration of a laryngoscopic tracheoscope in accordance with embodiments disclosed herein, illustrating alternate configurations of a distal portion of a tracheoscope member as controlled by a curving or steering mechanism via actuation of a steering assembly;

FIG. 9 schematically illustrates a portion of a prior art laryngoscope, showing a communication interface for communication with a camera;

FIG. 10 is a schematic illustration of the rear aspect of a portion of the laryngoscopic tracheoscope of FIG. 2, showing a communication interface and a steering assembly, a portion of a deformable cover, and indicating an optional wall cutout for a partial lumen for passage of a tracheoscope member and endotracheal tube;

FIG. 11 is a schematic illustration showing various graphical display devices that can be utilized, including a device screen, a portable screen, and a television screen, with screen interfaces and a communication interface facilitating display of laryngoscopic tracheoscope camera images;

FIG. 12 is a schematic illustration of a rear view of a portion of the laryngoscopic tracheoscope of FIG. 2, illustrating various aspects and structures, in accordance with embodiments disclosed herein;

FIG. 13 is a schematic illustration of a side view of the laryngoscopic tracheoscope of FIG. 2, illustrating various aspects and structures, in accordance with embodiments disclosed herein;

FIG. 14 is a schematic illustration showing the laryngoscopic tracheoscope being used for placement of an endotracheal tube within the trachea of a patient, after advancement into the airway of the patient, and with the endotracheal tube balloon inflated within the trachea;

4

Figure 16:
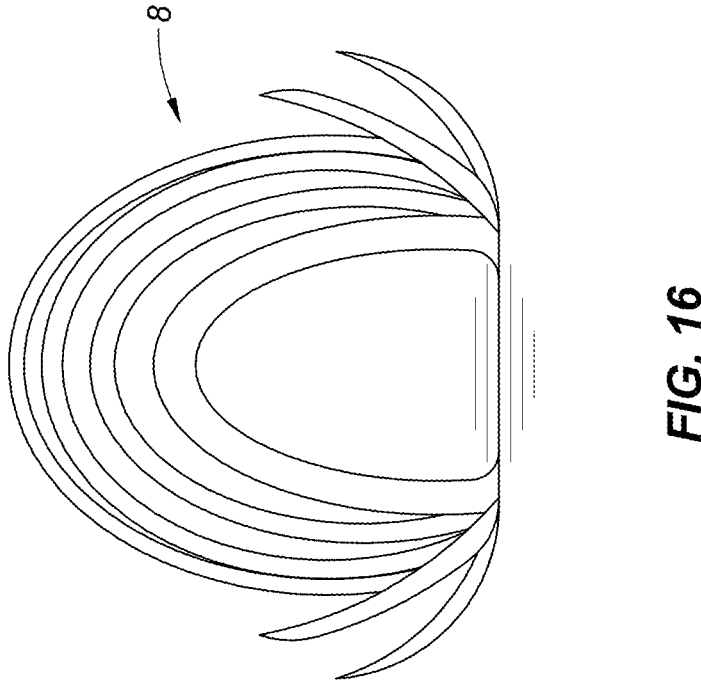
Figure 15:
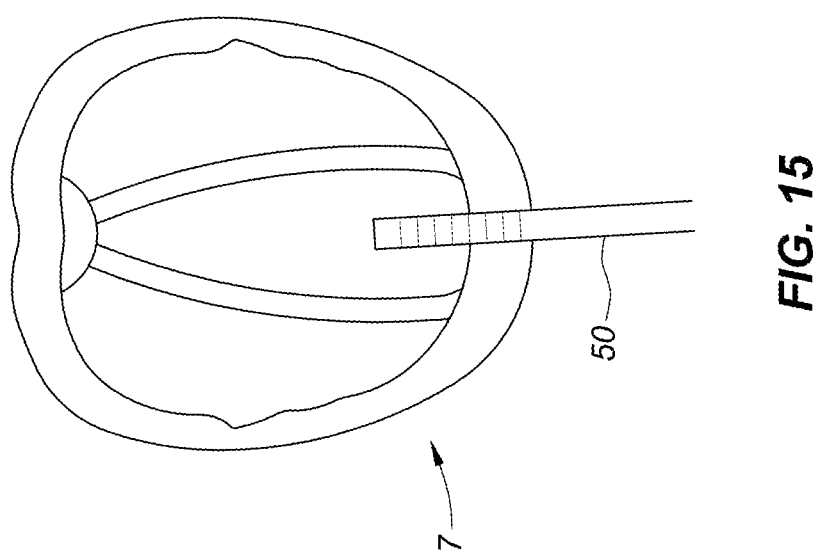
Figure 17:
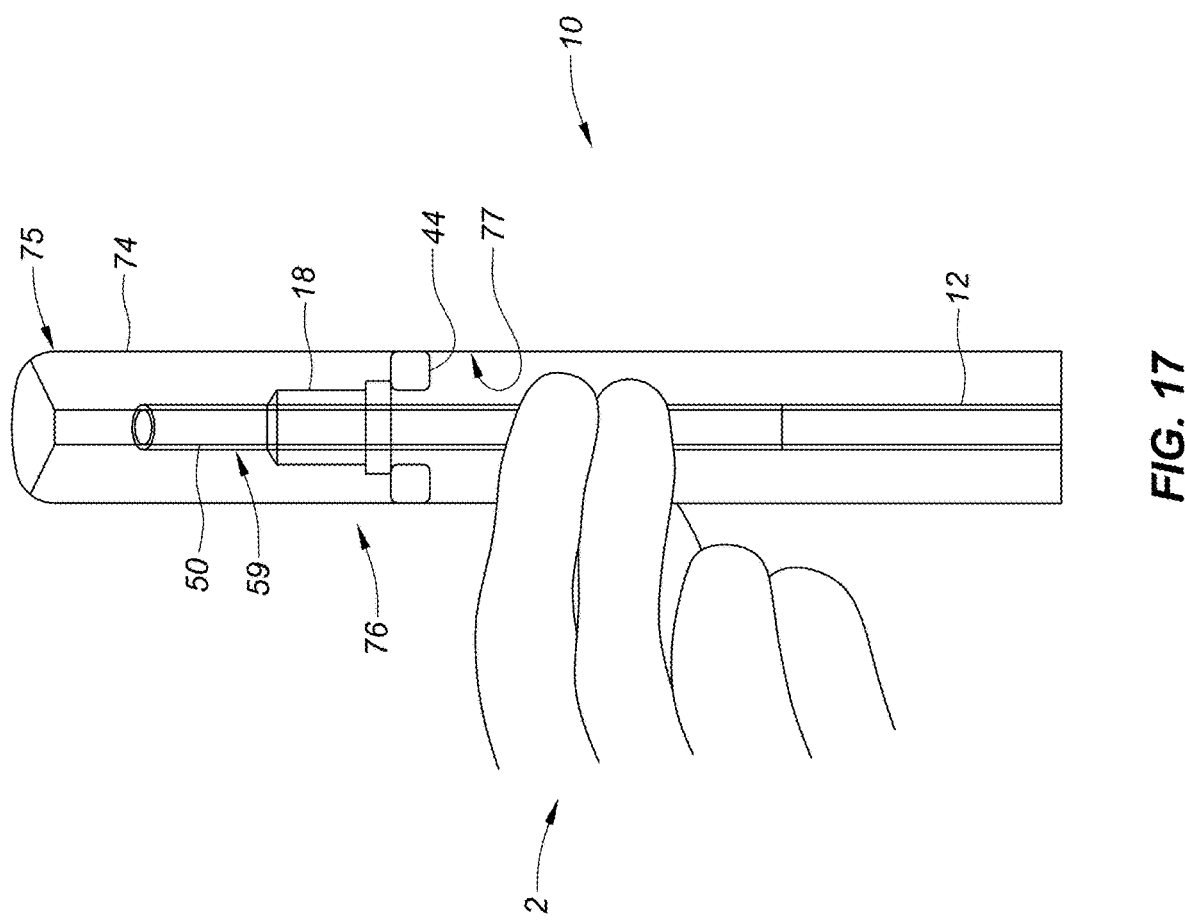
Figure 18:
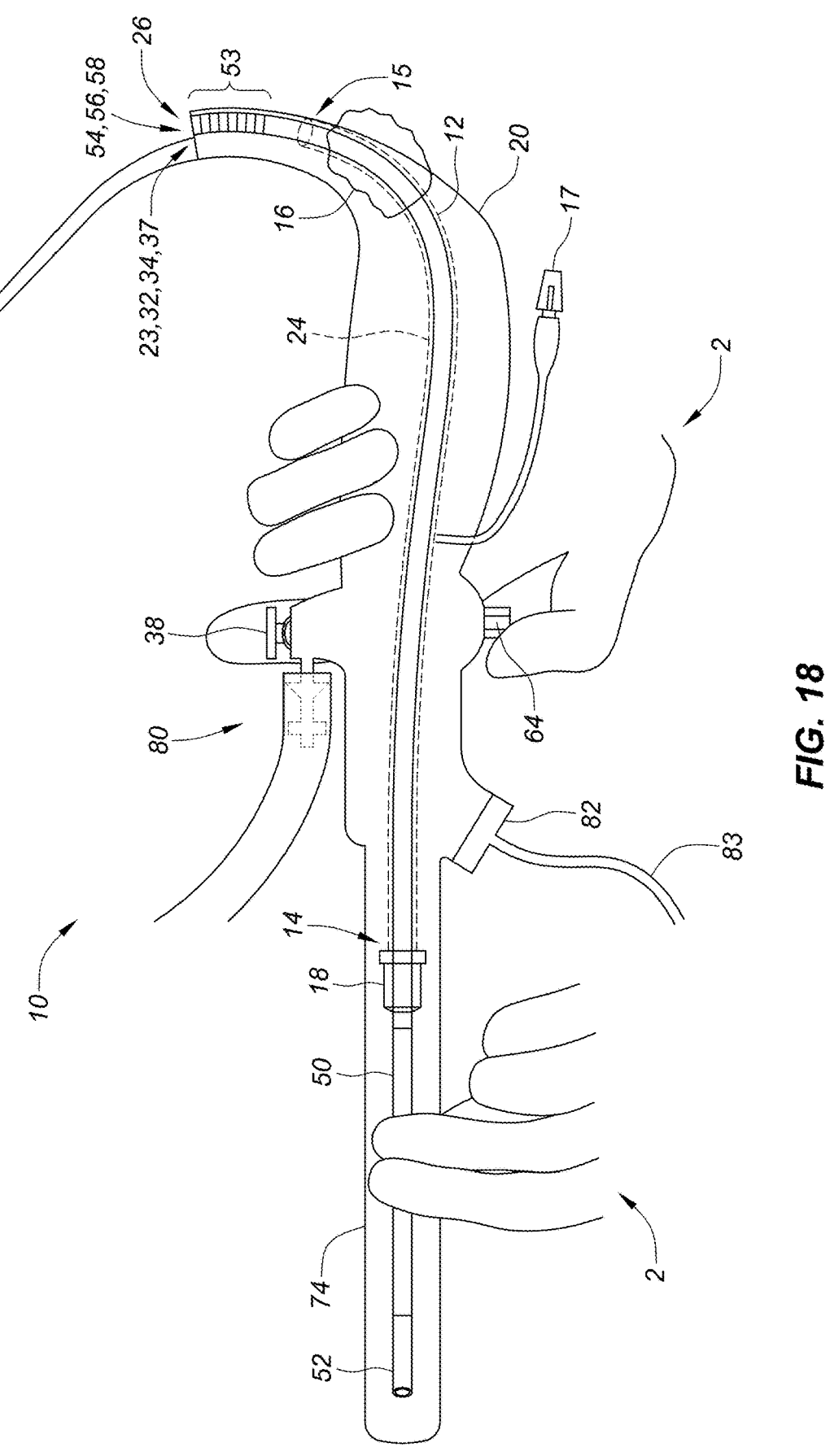
Figure 20:
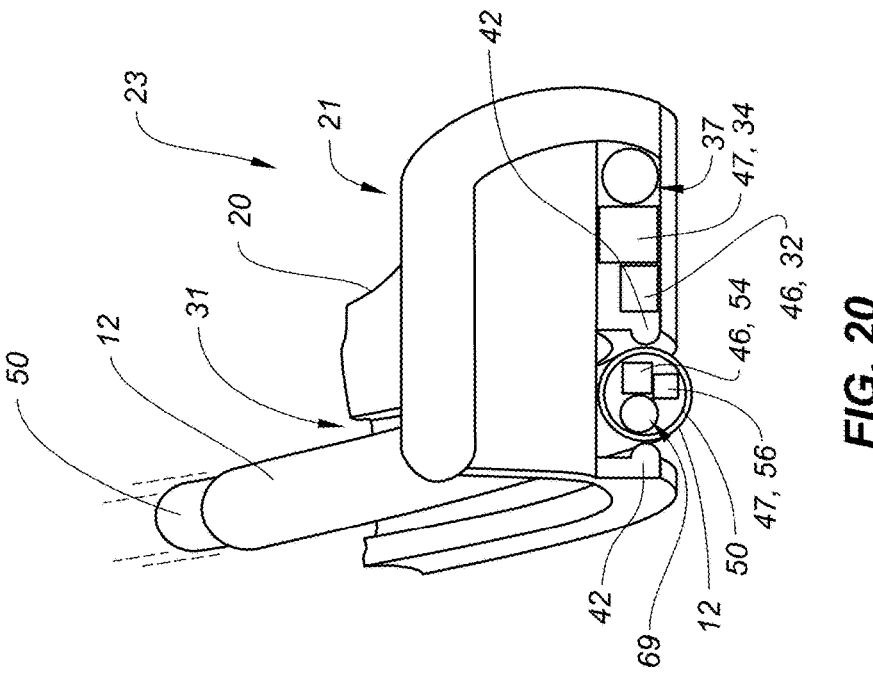
Figure 19:
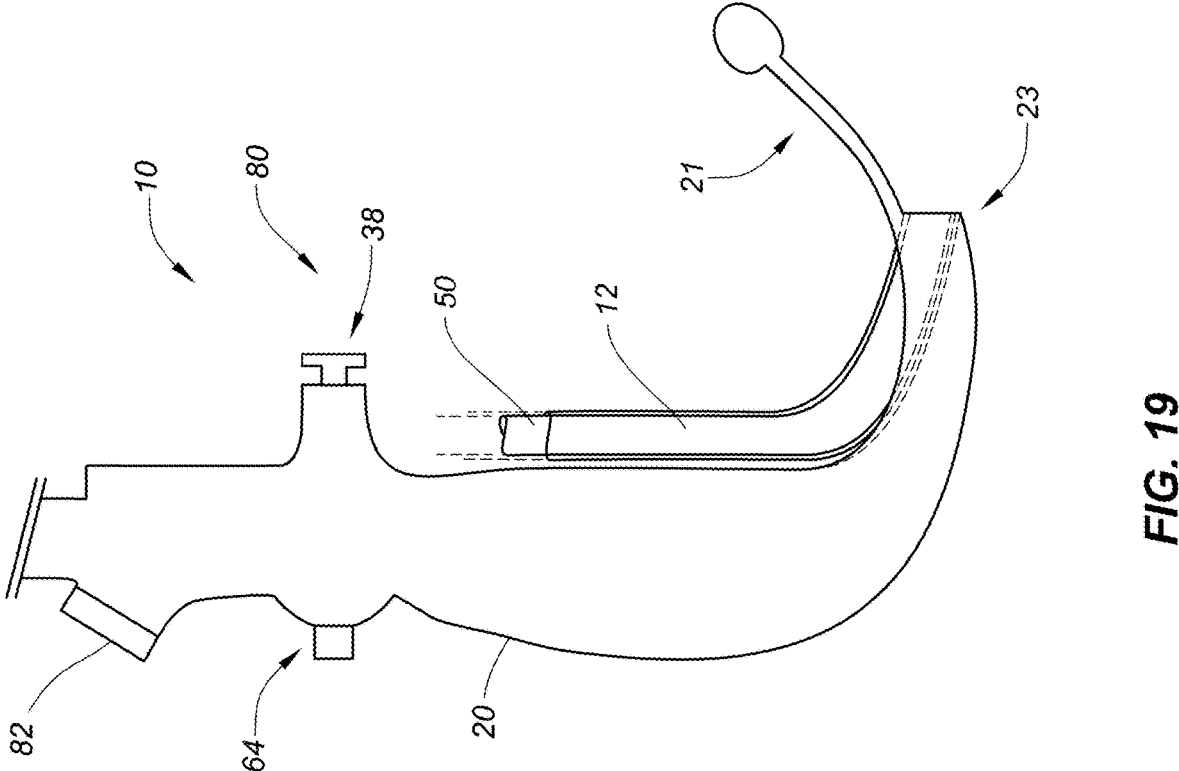
Figures 21, 22:
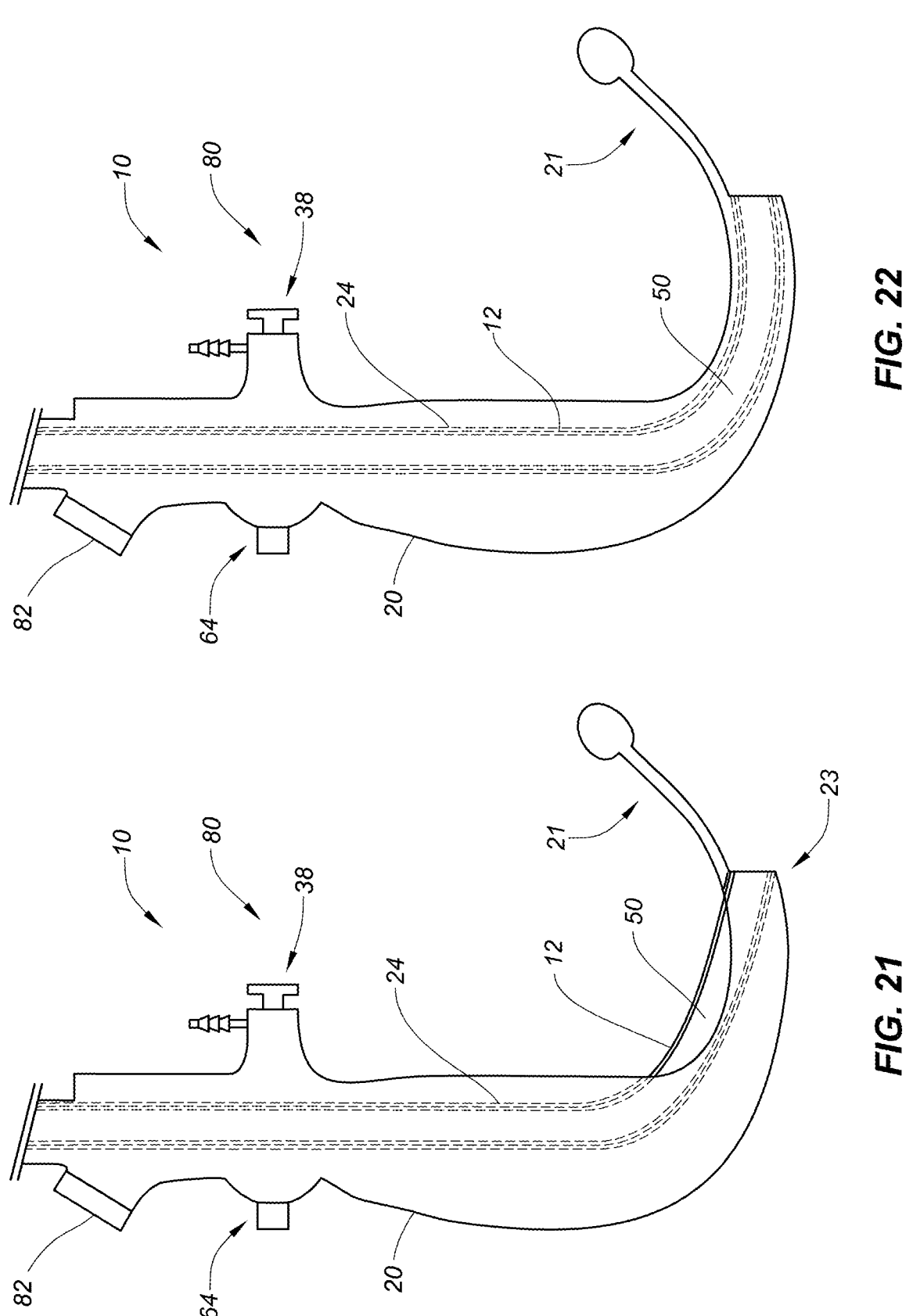

FIG. 15 is a schematic illustration showing the tracheoscope member being advanced through the patient's larynx, as viewed from a camera at the distal portion of the laryngoscope;

FIG. 16 is a schematic illustration showing the vocal cords of the patient as the tracheoscope member is advanced through the vocal cords, as viewed from a camera at the distal portion of the tracheoscope member;

FIG. 17 is a schematic illustration of a portion of the laryngoscopic tracheoscope, showing the user manipulating the endotracheal tube by deforming the deformable cover to contact the endotracheal tube and advancing the endotracheal tube distally;

FIG. 18 is a schematic side view of the laryngoscopic tracheoscope of FIG. 2, showing a user grasping the laryngoscope member, and manipulating the steering assembly and the suction actuator, and grasping the tracheoscope member via the deformable cover;

FIG. 19 is a schematic side view illustration of a laryngoscopic tracheoscope in accordance with embodiments disclosed herein, showing a tracheoscope member disposed within a cutout portion of the laryngoscope member;

FIG. 20 is a schematic front view of a distal portion of a laryngoscopic tracheoscope in accordance with embodiments disclosed herein, similar to that of FIG. 19, showing the tracheoscope member disposed within the cutout portion of the laryngoscope member, and illustrating cameras, lights, and suction apertures FIG. 21 is a schematic side view illustration of a laryngoscopic tracheoscope in accordance with embodiments disclosed herein, showing a tracheoscope member disposed within a cutout portion of the laryngoscope member and extending proximally within a first lumen of the laryngoscope member; and FIG. 22 is a schematic side view illustration of a laryngoscopic tracheoscope in accordance with embodiments disclosed herein, showing a tracheoscope member disposed within a first lumen of the laryngoscope member.

DETAILED DESCRIPTION

Now referring to the drawings, which illustrate various aspects of embodiments disclosed in the present disclosure and distinguish the embodiments disclosed herein from the prior art, we note that some items are schematically illustrated in views where they might not be visible, in order to more clearly show the structure and relationship of elements and simplify presentation to the reader. In some views, elements and features that could potentially be shown in dashed or hatched form or sectioned or exploded views are instead schematically illustrated as if potentially obscuring elements or portions of elements are transparent. In other views, portions of some elements are illustrated, with the understanding that other portions are not shown, for clarity of illustration. By a full viewing of the various figures and text herein, the structure and function of embodiments disclosed herein are disclosed, notwithstanding these simplifications.

Prior art laryngoscopes typically are shaped similar to that schematically illustrated in FIG. 1, which schematically illustrates prior art laryngoscope 90, and can be used to facilitate insertion of an endotracheal tube (ETT) in an airway of a patient. A user may utilize a light to aid in insertion of the endotracheal tube. Some prior art laryngoscopes include imaging aids such as lenses, lights, and/or cameras. Currently, prior art laryngoscopes commonly include a video camera and a light, and graphical display screen to aid the user in negotiating proper placement of an endotracheal tube or in other diagnostic or therapeutic procedure. Laryngoscopes are available that have a variety of distal "blade" sizes and shapes to accommodate varied patient anatomy.

Some embodiments disclosed herein include a video laryngoscopic tracheoscope or laryngoscopic tracheoscope 10, that includes additional structures and functions not found in prior art laryngoscopes. The laryngoscopic tracheoscope 10 can be used by a physician, nurse, emergency personnel, veterinary personnel, or other user 2 to facilitate a diagnostic or therapeutic procedure such as examination of a body cavity, and particularly for placement of an endotracheal tube 12. Some embodiments disclosed herein include the laryngoscopic tracheoscope 10, a portion of which is schematically illustrated in FIG. 2, which shows a tracheoscope member 50 disposed within a laryngoscope member 20. Some internal elements are schematically illustrated in FIG. 2 to indicate their general position or structure, even though they may be hidden within or behind other structures of the laryngoscope member 20. Other portions and elements are as described elsewhere herein. The tracheoscope member 50 includes a tracheoscope proximal portion 52 (FIG. 3) and a tracheoscope distal portion 53 (FIG. 6). The laryngoscope member 20 includes a first lumen 24 for passage of the tracheoscope member 50. In some embodiments, the first lumen 24 is configured for passage of the tracheoscope member 50 together with the endotracheal tube 12, as depicted in FIG. 3. The endotracheal tube 12 includes an endotracheal tube proximal portion 14 and an endotracheal tube distal portion 15. In some embodiments, the first lumen 24 is a continuous lumen extending along the laryngoscope member 20 between a laryngoscope proximal portion 22 and a laryngoscope distal portion 23. In some embodiments, the first lumen 24 includes one or more lumen segments arranged along the laryngoscope member 20, so that portion(s) of the tracheoscope member 50 are located within the first lumen 24, and portion(s) of the tracheoscope member 50 are located outside but adjacent to the laryngoscope member 20. The first lumen 24 has a distal aperture 26 through which the tracheoscope distal portion 53 and the endotracheal tube distal portion 15 can be advanced. The laryngoscope member 20 includes a blade portion 21 configured for negotiating the airway 6 of the patient 4.

In some embodiments, the laryngoscopic tracheoscope 10 can include a suction system 80 to provide suction for the tracheoscope member 50 and/or the laryngoscope member 20. In some embodiments, the laryngoscope member 20 includes a laryngoscope suction lumen 36 that communicates from a suction manifold 40 to a distal laryngoscope suction aperture 37 located near a laryngoscope camera 32. In some embodiments, the tracheoscope member 50 includes a tracheoscope suction lumen 68 that communicates from the suction manifold 40 to a distal tracheoscope suction aperture 69 located near a tracheoscope camera 54. In some embodiments, the suction system 80 is configured for attachment to a suction device such as a syringe, vacuum pump, bulb, wall suction, etc., to supply suction via the tracheoscope suction lumen 68 and distal tracheoscope suction aperture 69 and/or the laryngoscopy suction lumen 36 and distal laryngoscope suction aperture 37 to clear unwanted material from the tracheoscope camera 54 and/or the laryngoscope camera 32, respectively. In other embodiments, the suction system 80 is instead configured for attachment to a fluid supply such as a syringe, pump, bulb, air supply, oxygen supply, saline supply, etc., to blow or spray via the tracheoscope suction lumen 68 and distal tracheoscope suction aperture 69 and/or the laryngoscopy suction lumen 36 and distal laryngoscope suction aperture 37 to clear unwanted material from the tracheoscope camera 54 and/or the laryngoscope camera 32, respectively. In still other embodiments, the suction system 80 can be used to apply suction or fluid flow alternatively or intermittently as desired to clear unwanted material from the tracheoscope camera 54 and/or the laryngoscope camera 32.

In some embodiments, the laryngoscopic tracheoscope 10 includes electrical wires 83 and one or more electrical connections such as communication interface 82 which can provide for a light (such as laryngoscope light 34) and/or camera (such as laryngoscope camera 32) disposed at the laryngoscope distal portion 23 and/or for a light (such as tracheoscope light 56) and/or camera (such as tracheoscope camera 54) disposed at the tracheoscope distal portion 53.

As further depicted in FIG. 2, some embodiments of the laryngoscopic tracheoscope 10 includes a steering assembly 64 that provides control of ante/retroflexion of the tracheoscope distal portion 53; the steering assembly 64 may also be referred to herein as a curving mechanism. In some embodiments, one or more pullwires 60 are coupled with the steering assembly 64 and extend proximally along the laryngoscopic tracheoscope 10 and distally along the tracheoscope member 50, as schematically illustrated in FIG. 2. The steering assembly 64 can be actuated by the user 2 to flex or straighten the tracheoscope distal portion 53 as desired, allowing the tracheoscope member 50 to be directed along the patient's airway 6 for example, or to direct the tracheoscope camera 54 as desired.

In some embodiments, the endotracheal tube 12 and the tracheoscope member 50 can be coupled to an exterior portion of the laryngoscope member 20, as illustrated in FIG. 3, which shows a laryngoscope member 20 loaded with a tracheoscope member 50 and endotracheal tube 12, in which the first lumen 24 is coupled to the exterior portion of the laryngoscope member 20; the first lumen 24 can be a separate tube that is secured to the laryngoscope member 20 along a substantial portion of its length, or attached a discrete points by adhesive, shrink-wrap material, tape, or other attachment elements 28. In the example illustrated in FIG. 3, the first lumen 24 is coupled to the laryngoscope member 20 by an adhesive polymer material or tape attachment elements 28. In some embodiments, the first lumen 24 extends further proximally than the laryngoscope proximal end 22a. FIG. 3 illustrates portions of the laryngoscopic tracheoscope 10; some embodiments of the laryngoscopic tracheoscope 10 further include a deformable cover 74 (see FIGS. 12, 14, 18 and elsewhere herein).

The prior-art laryngoscope 90 of FIG. 1 may have a camera 92 and light 94 at the distal portion of the laryngoscope 90, such as is illustrated in FIG. 4. Such prior art laryngoscope camera 92 can have obstructed views due to saliva, phlegm, or other unwanted material interfering with the camera 92 and/or light 94.

Some embodiments of the present laryngoscopic tracheoscope 10 include camera apparatus 46. In some embodiments, the camera apparatus 46 includes a laryngoscope camera 32 disposed at the laryngoscope distal portion 23, and/or a tracheoscope camera 54 disposed at the tracheoscope distal portion 53. Some embodiments of the laryngoscopic tracheoscope 10 include light apparatus 47. The light apparatus 47 includes a light disposed to illuminate at least a portion of the patient 4 (FIG. 14) viewed by the camera apparatus 46. In some embodiments, the light apparatus 47 includes a tracheoscope light 56 arranged to illuminate at least a portion of the patient 4 viewed by the tracheoscope camera 54 and a laryngoscope light 34 arranged to illuminate at least a portion of the patient 4 viewed by the laryngoscope camera 32. In some embodiments, the laryngoscopic tracheoscope 10 includes a laryngoscope camera 32 and corresponding laryngoscope light 34 and a distal laryngoscope suction aperture 37 at the laryngoscope distal portion 23, as well as a tracheoscope camera 54 and corresponding tracheoscope light 56 and a distal tracheoscope suction aperture 58 at the tracheoscope distal portion 53, as shown in FIG. 5, which schematically illustrates part of the tracheoscope distal portion 53 disposed in the first lumen 24 of the laryngoscope member 20. The distal laryngoscope suction aperture 37 and/or the distal tracheoscope suction aperture 58, when connected to a suction line or suction supply line 81 and actuated by the user 2 via the suction actuator 38, act to clear the respective camera (32, 54) and light (34, 56) of unwanted obstructive material such as secretions, gastric contents, and/or blood so that the camera view is improved. In some embodiments of the laryngoscopic tracheoscope 10 consistent with the disclosure herein, the tracheoscope camera 54 is arranged proximate the laryngoscope camera 32 so that the images viewed from the tracheoscope camera 54 and the laryngoscope camera 32 are consistent with each other. In some embodiments of the laryngoscopic tracheoscope 10 consistent with the disclosure herein, the laryngoscope member 20 includes distal tracheoscope retainer 42 to engage and stabilize the tracheoscope member 50 while allowing the tracheoscope member 50 to be manipulated as needed to conduct the diagnostic or therapeutic procedure being performed.

In some embodiments, the tracheoscope member 50 can be advanced distally with respect to the laryngoscope member 20, and the laryngoscope camera 32 and corresponding laryngoscope light 34 on the laryngoscope distal portion 23 can be utilized to provide a view of the tracheoscope member 50 being advanced. The laryngoscope camera 32, laryngoscope light 34 and distal laryngoscope suction aperture 37, and the tracheoscope camera 54, tracheoscope light 56, and distal tracheoscope suction aperture 69, can be utilized separately or in concert to facilitate the particular diagnostic or therapeutic procedure being performed, such as examination of the airway 6, or placement of an endotracheal tube 12 in the airway 6 of the patient 4.

FIG. 6 schematically illustrates portions of a laryngoscopic tracheoscope 10 consistent with embodiments disclosed herein. The laryngoscope member 20 is shown with the tracheoscope member 50 and the endotracheal tube 12 loaded within the first lumen 24, and further illustrates the user 2 grasping the laryngoscopic tracheoscope 10, actuating the suction actuator 38 to apply suction from the attached suction line 81, actuating the steering assembly 64 to flex or straighten the tracheoscope distal portion 53 as desired, and also illustrates the communication interface 82, and an endotracheal tube balloon inflation port 17 that provides for inflation of the endotracheal tube balloon 16 when the user 2 has positioned the endotracheal tube 12 as desired. For clarity of illustration, only a portion of the inflation lumen that extends from the balloon inflation port 17 to the balloon 16 has been depicted. As disclosed herein, suction can be provided for the tracheoscope distal portion 53 and/or for the laryngoscope distal portion 23. In some embodiments, a suction manifold 40, can be included to supply suction to both the laryngoscope member 20 and the tracheoscope member 50. In some embodiments, the suction manifold 40 can be proximate the suction actuator 38, such as further depicted in the example in FIG. 2. In some embodiments, the laryngoscopic tracheoscope 10 can include the communication interface 82 to provide for viewing a video feed from a tracheoscope camera 54 (FIG. 5) disposed at the tracheoscope distal portion 53 and/or a laryngoscope camera 32 (FIG. 5) disposed at the laryngoscope distal portion 23, allowing the imaging to be viewed on a graphical display screen.

FIG. 7 is a schematic illustration of a proximal portion of the laryngoscopic tracheoscope 10 in accordance with some embodiments disclosed herein, with an endotracheal tube 12 loaded onto the tracheoscope member 50 that is loaded within the first lumen 24 of the laryngoscope member 20, further showing the deformable cover 74 enclosing the tracheoscope proximal portion 52, with the tracheoscope member 50 being manipulated through the deformable cover 74. In some embodiments, the proximal portion of the laryngoscopic tracheoscope 10 includes the deformable cover 74, which has an elongated structure with a deformable cover proximal portion 75 and a deformable cover distal portion 76, and extends proximally from the laryngoscope proximal portion 22 (see also FIG. 12, for example). In some embodiments, the tracheoscope member 50 and the endotracheal tube 12 are disposed within the deformable cover 74. In some embodiments, the deformable cover 74 is a sleeve that defines a covered lumen that extends along the deformable cover 74. In some embodiments, the deformable cover 74 includes a closed deformable cover proximal end 75a, and an open deformable cover distal end 76a which can be attached to a proximal end 22a of the laryngoscope member 20. In some embodiments, a passageway can be defined from the closed deformable cover proximal end 75a, along the deformable cover 74, and along the first lumen 24, through the laryngoscope member 20 to the distal aperture 26. In use, a physician can grasp the deformable cover 74 and partially collapse the deformable cover 74, such that a deformable cover inner surface 77 contacts a tracheoscope outer surface 59 and thereby grips the tracheoscope member 50, allowing the tracheoscope member 50 to be advanced through the endotracheal tube 12 and out a laryngoscope distal end 23a. The deformable cover 74 can also house portions of a suction line 81, electrical wires 83, and pullwires 60 associated with the tracheoscope member 50. The user 2 can thus grip the deformable cover 74 and advance the tracheoscope member 50, and associated suction line 81, electrical wires 83, and pullwires 60 towards the laryngoscope distal portion 23, and if desired, advance the tracheoscope distal portion 53 distally out through the distal aperture 26. The deformable cover 74 can aid in managing the various power, signal, and control wires such as electrical wires 83 in communication with the tracheoscope member 50, as well as the steering pullwires 60 and suction line 81 for the tracheoscope member 50, while facilitating manipulation of the tracheoscope member 50 by the user 2.

In some embodiments, the laryngoscopic tracheoscope 10 includes a retainer portion 44 that contacts an endotracheal tube stop portion 18 to limit distal advancement of the endotracheal tube 12, as schematically illustrated in FIG. 7. The retainer portion 44 can contact a portion of the endotracheal tube stop portion 18 such as wings or other protrusions of the endotracheal tube stop portion 18, preventing the endotracheal tube 12 from being inadvertently advanced when the tracheoscope member 50 is advanced. When the user 2 desires to advance the endotracheal tube 12 distally out of the distal aperture 26 to position the endotracheal tube 12 in the patient's airway 6, the user 2 applies additional force to advance the endotracheal tube stop portion 18 past the retainer portion 44. In some embodiments, one or both of the retainer portion 44 and the endotracheal tube stop portion 18 are formed from a deformable material, thereby allowing for deformation of one or more of the retainer portion 44 and the stop portion 18, as the stop portion 18 is advanced through the retainer portion 44. When the user 2 desires to advance the endotracheal tube 12 past point at which the retainer portion 44 contacts the endotracheal tube stop portion 18, the user 2 can grip the endotracheal tube 12 through the deformable cover 74 distal to the retainer portion (see FIG. 17) and advance the endotracheal tube 12. Some embodiments do not require the retainer portion(s) 44 or the endotracheal tube stop portion 18. In some embodiments the retainer portion 44 is a close-fitting portion that provides limited resistance to advancement of the endotracheal tube 12, but which can be overcome by the user 2 applying moderate advancing force to the endotracheal tube 12.

When the tracheoscope member 50 is advanced distally by the user 2 so that the tracheoscope distal portion 53 has exited the distal aperture 26, the user 2 is able to actuate the steering assembly 64 to flex or straighten the tracheoscope distal portion 53 as desired, as schematically illustrated in FIG. 8, which shows 3 example bend configurations 66*a*, 66*b*, 66*c* of the tracheoscope distal portion 53, corresponding to straight, anteflexion and retroflexion configurations of the tracheoscope distal portion 53. By actuating the steering assembly 64, the user 2 can orient the tracheoscope distal portion 53 to direct the tracheoscope camera 54 as desired, and can direct the tracheoscope member 50 in a desired direction for advancement and positioning within the airway 6 of the patient 4.

FIG. 9 depicts a portion of a prior art laryngoscope 90, such as the prior-art laryngoscope 90 of FIG. 1, which may have a communication interface 96 to provide connection to a camera 92 and light 94 at the distal portion of the laryngoscope 90, if so equipped, such as is illustrated in FIG. 9. Obstruction of camera views such as due to saliva, phlegm, or other unwanted material interfering with the camera, remains a problem with such prior art laryngoscopes.

A portion of some embodiments of the laryngoscopic tracheoscope 10 of FIG. 2 is schematically illustrated in FIG. 10, which depicts a rear view showing the steering assembly 64 and a communication interface 82. In some embodiments, such as illustrated in FIG. 10, a portion of the laryngoscope member 20 has been "cut away", leaving portions of the tracheoscope member 50 and/or the endotracheal tube 12 outside and adjacent to the laryngoscope member 20. A grooved portion 30, for example can be incorporated for passage of the tracheoscope member 50 and/or the endotracheal tube 12 in order to minimize the size and bulk of the laryngoscope member 20 and facilitate placement within the mouth and airway 6 of the patient 4. The tracheoscope member 50 and/or the endotracheal tube 12 can be grasped by the user 2 in this cut-away portion 29, to control the motion and position of the tracheoscope member 50 and/or the endotracheal tube 12. The cut-away portion 29 or grooved portion 30 or cutout portion 31 (FIG. 20) can be arranged nearer one side or the other of the laryngoscope member 20, or nearer the front or the rear of the laryngoscope member 20, to facilitate introduction and manipulation of the tracheoscope member 50 and the endotracheal tube 12. In other embodiments disclosed herein, the first lumen 24 is continuous, extending between the laryngoscope proximal portion 22 and the laryngoscope distal portion 23, such as is schematically illustrated in FIG. 2. In FIGS. 10 and 11, a deformable cover 74 is illustrated; in other embodiments, the cut-away portion 29 is sufficient for manipulation of the tracheoscope member 50 and the endotracheal tube 12, so that a deformable cover 74 may not needed to provide for manipulation of the tracheoscope member 50 and endotracheal tube 12. In such situations, a similar cover could be utilized to maintain arrangement of elements such as the pullwires 60, the suction line 81, electrical wires 83, and the like; in some embodiments, a more rigid cover (not shown), or other protective sleeve, or no cover, can be used instead of the deformable cover 74 illustrated. In some embodiments, the tracheoscope member 50 and the deformable cover 74 extend proximally from the one side, such as the left side, of the laryngoscope proximal portion 22 to facilitate convenient manipulation of the laryngoscope member 20 and the tracheoscope member 50.

Various graphical user interfaces (GUIs) 84 and graphical displays 86 can be utilized with the present laryngoscopic tracheoscope 10, including those schematically illustrated in FIG. 11, which illustrates a portion of the laryngoscopic tracheoscope 10. The GUIs and graphical displays can include a laryngoscope device screen 86*a* attached to the laryngoscope member 20, a tracheoscope device screen 86*b* attached to the tracheoscope member 50, a portable screen 86*c*, a television screen 86*d*, a computer/monitor screen 86*e*, etc., or a combination of elements such as these, which can all be coupled to the laryngoscopic tracheoscope 10 via the communication interface 82. The GUIs 84 can include user selectable inputs and controls for the cameras 32, 54, lights 34, 56, suction system, 80, or other elements, or provide status information regarding elements of the laryngoscopic tracheoscope 10, or other information relevant to the procedure being performed by the user 2. The communication interface 82 can provide for connection and disconnection of elements of the laryngoscopic tracheoscope 10 described herein, such as to transmit power or signal between the elements, either by the user 2 or during an assembly process. Alternatively, the communication interface 82 can include pre-assembled wires connecting elements and not intended for disconnection by the user 2. In some embodiments, the communication interface can include aspects that are user-operable and other aspects that are not user-operable, such as signal passage via wires, and power access that is connectable and disconnectable by the user 2. In some embodiments, power can be provided by an on-board power source such as a battery or the like. In some embodiments, the communication interface 82 can include wireless communication elements, or a combination of wired and wireless communication elements.

Electrical wires 83 for the laryngoscope member 20 and the tracheoscope member 50 are schematically illustrated in FIG. 12, connecting the communication interface 82 with the laryngoscope camera 32 and the tracheoscope camera 54. Other elements are also illustrated, as discussed herein, including the steering assembly 64, the pullwires 60, the suction line 81, and so forth. In some embodiments disclosed herein, the deformable cover 74 accommodates the proximal portion of the tracheoscope member 50 and can be manually compressed to manipulate the tracheoscope member 50.

In some embodiments, a pullwire pulley 62 is incorporated to provide for a direction-change of the pullwires 60 so that the steering assembly 64 can be located near the laryngoscope proximal portion 22, rather than at the tracheoscope proximal portion 52, which may be enclosed within the deformable cover 74 in some embodiments, such as is schematically illustrated in FIG. 13. Thus, the user manipulation and actuation elements can all be located for convenient manipulation and actuation, in close proximity to each other, so that the user 2 may be able to grasp the laryngoscope member 20, and easily reach the steering assembly 64 and the suction actuator 38, as also illustrated in FIG. 6. Various features associated with the laryngoscopic tracheoscope 10 as disclosed herein are depicted in FIG. 13, in accordance with embodiments of the present disclosure. In the example embodiment illustrated in FIG. 13, the deformable cover distal end 76a can be connected to the proximal portion of the laryngoscope member 20 as illustrated, with the tracheoscope member 50 loaded within the deformable cover 74, ready for advancement by the user 2 by grasping and pushing the tracheoscope member 50 towards the laryngoscope distal portion 23.

FIG. 14 schematically illustrates advancement of the laryngoscopic tracheoscope 10 down a patient's larynx 7, into their trachea 9. In some embodiments, the tracheoscope member 50 is loaded into the endotracheal tube 12 as illustrated. In some embodiments, the laryngoscope camera 32, the tracheoscope camera 54, and manipulation of the laryngoscopic tracheoscope 10 can be used to position the endotracheal tube 12 in the desired location. In some embodiments, after positioning the endotracheal tube 12 as desired, the endotracheal tube balloon 16 can be inflated as illustrated, and the tracheoscope member 50 and laryngoscope member 20 withdrawn and removed, thus providing for intubation of the patient 4. Air, oxygen, inhalation anesthetics, medications, or other materials can be introduced through the endotracheal tube 12 for delivery to the airway 6 of the patient 4.

As the tracheoscope member 50 is advanced through the patient's larynx 7, a view such as that schematically illustrated in FIG. 15 can be visualized using the laryngoscope camera 32. In FIG. 15, the tracheoscope member 50 is seen passing through a patient's vocal cords 8.

In FIG. 16, the vocal cords 8 of the patient 4 are schematically illustrated as they would be viewed by the tracheoscope camera 54 as the tracheoscope member 50 is being advanced through the patient's vocal cords 8.

In embodiments that include the deformable cover 74, advancement of the endotracheal tube 12 is schematically illustrated in FIG. 17, which shows the user 2 grasping the deformable cover 74 with enough force to deform the deformable cover 74 and cause contact between the deformable cover inner surface 77 and the tracheoscope outer surface 59 and/or the endotracheal tube 12. The user 2 can then pull downward in a distal direction with sufficient force to cause the endotracheal tube stop portion 18 to be advanced past the retainer portions.

The tracheoscope member 50, including in some embodiments the tracheoscope camera 54, tracheoscope light 56, and distal tracheoscope suction aperture 58, can be advanced to and out of the distal aperture 26 of the first lumen 24 of the laryngoscope member 20 as schematically illustrated in FIG. 18. Various other elements of the laryngoscopic tracheoscope 10 are also shown on FIG. 18 as disclosed herein, including the laryngoscope distal portion 23, the laryngoscope camera 32, the laryngoscope light 34, the distal laryngoscope suction aperture, the tracheoscope distal portion 53, the endotracheal tube 12, the endotracheal tube distal portion 15, the endotracheal tube balloon 16, the endotracheal tube balloon inflation port 17, the first lumen 24, the endotracheal tube proximal portion 14, the endotracheal stop portion 18, the tracheoscope proximal portion 52, the deformable cover 74, the suction system 80, the suction actuator 38, the steering assembly 64, the communication interface 82, and electrical wires 83. In some of the figures, the endotracheal tube balloon 16 is illustrated in an exaggerated shape to emphasize that the structure is a balloon; during passage through the first lumen 24, and initial positioning within the airway 6 of the patient 4, the endotracheal tube balloon 16 would preferably be completely deflated to provide for such passage and positioning.

A portion of some embodiments of the laryngoscopic tracheoscope 10 of FIG. 2 is schematically illustrated in FIG. 19, which depicts a rear view showing the steering assembly 64 and a communication interface 82. In some embodiments, such as illustrated in FIG. 19, laryngoscope member 20 includes a cutout portion 31, providing access for positioning the tracheoscope member 50 partially within the laryngoscope member 20. In the illustrated embodiment, portions of the tracheoscope member 50 and/or the endotracheal tube 12 are disposed outside and adjacent to the laryngoscope member 20, and portions of the tracheoscope member 50 and/or the endotracheal tube 12 are disposed inside the laryngoscope member. The tracheoscope member 50 and/or the endotracheal tube 12 can be grasped by the user 2 where they are disposed outside of the laryngoscope member 20, to control the motion and position of the tracheoscope member 50 and/or the endotracheal tube 12 independently of the laryngoscope member 20. The tracheoscope member 50 and/or the endotracheal tube 12 can be withdrawn or advanced relative to the laryngoscope member 20 as needed. In embodiments of the laryngoscopic tracheoscope 10 illustrated in FIG. 20, the laryngoscope member 20 includes distal tracheoscope retainer 42 to engage and stabilize the tracheoscope member 50 while allowing the tracheoscope member 50 to be manipulated as needed to conduct the diagnostic or therapeutic procedure being performed.

In some embodiments, such as illustrated in FIG. 20, which shows a front view of a portion of the laryngoscopic tracheoscope 10 similar to that illustrated in FIG. 19, the tracheoscope member 50 is disposed within the cutout portion 31 of the laryngoscope member 20, and includes camera apparatus 46, light apparatus 47, distal laryngoscope suction aperture 37, and distal tracheoscope suction aperture. In the embodiments illustrated in FIG. 20, the laryngoscope member 20 includes a laryngoscope camera 32 and corresponding laryngoscope light 34 and a distal laryngoscope suction aperture 37, and the tracheoscope member 50 includes a tracheoscope camera 54 and corresponding tracheoscope light 56 and a distal tracheoscope suction aperture 58, lights, and suction apertures. Only portions of the laryngoscopic tracheoscope 10 are illustrated in FIGS. 19 and 20, with other portions and elements as described elsewhere herein. Also, in the schematic illustrations of FIGS. 19 and 20, some elements are shown to schematically illustrate their position or structure, even though they may be hidden within or behind other structures.

In various embodiments of the laryngoscopic tracheoscope 10 in accordance with embodiments disclosed herein, there is provided the first lumen 24, the lumen segment(s) 28, the cut-away portion 29, the grooved portion 30, the cutout portion 31, or similar structure for passage of the tracheoscope member 50 within, coupled to, or together with the laryngoscope member 20, so that the laryngoscopic tracheoscope 10 includes the camera apparatus 46, the light apparatus 47, and portions of the suction system 80, as such as described herein. Consistent with embodiments disclosed herein, the tracheoscope member 50, including the tracheoscope camera 54, the tracheoscope light 56, and the distal tracheoscope suction aperture 58, and the laryngoscope member 20, including the laryngoscope camera 32, the laryngoscope light 35, and the distal laryngoscope suction aperture 37, are manipulatable separately or in concert by the user 2, to facilitate the particular diagnostic or therapeutic procedure being performed, such as examination of the airway 6, or placement of the endotracheal tube 12 in the airway 6 of the patient 4.

For example, in the embodiment of the laryngoscopic tracheoscope 10 schematically illustrated in FIG. 21, which depicts a rear view similar to that of FIG. 19, a portion of the tracheoscope member 50 passes within the laryngoscope member 20, and a portion of the tracheoscope member 50 passes along the cutout portion 31, providing access for positioning the tracheoscope member 50 partially within the laryngoscope member 20. In the illustrated embodiment, portions of the tracheoscope member 50 and/or the endotracheal tube 12 are disposed outside and adjacent to the laryngoscope member 20, and portions of the tracheoscope member 50 and/or the endotracheal tube 12 are disposed inside the laryngoscope member. The tracheoscope member 50 and/or the endotracheal tube 12 can be grasped by the user 2 where they are disposed outside of the laryngoscope member 20, to control the motion and position of the tracheoscope member 50 and/or the endotracheal tube 12 independently of the laryngoscope member 20. The front view of a portion of the laryngoscopic tracheoscope 10 of FIG. 21 is similar to the view illustrated in FIG. 20.

In another example, in the embodiment of the laryngoscopic tracheoscope 10 schematically illustrated in FIG. 22, which depicts a rear view similar to that of FIGS. 19 and 21, the tracheoscope member 50 passes within the laryngoscope member 20. In this example, the proximal portion of the tracheoscope member 50 extends proximally from the laryngoscope proximal portion 22, providing access for positioning the tracheoscope member 50 as desired. The proximal portion of the tracheoscope member 50 may be disposed within the deformable cover 74 as described elsewhere herein. The front view of a portion of the laryngoscopic tracheoscope 10 of FIG. 22 is similar to the view illustrated in FIG. 20, except that the portions of the tracheoscope member 50 and the endotracheal tube 12 that are visible in FIG. 20 would be hidden within the laryngoscope member 20, and a hidden first lumen 24 would be located within the laryngoscope member 30 in place of visible portion of the cutout portion 31.

Various embodiments are described herein of various apparatus and/or systems. Numerous specific details are set forth to provide a thorough understanding of the overall structure, function, manufacture, and/or use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

As used herein, terms such as "inside", "outside", "inner", "outer", "height", "width" "thickness", "top", "bottom", "side", "above", "below", and so forth generally are used herein with their ordinary meaning, consistent with the drawings herein illustrating the embodiments disclosed herein. These general direction and orientation indications are used herein for clarity of presentation, but are not necessarily intended to be limiting. For example, the "width" of an element may be longer than the "length" of the element, and "height" may be used to describe a vertical dimension of an element, but still used if in some views or embodiments that element is oriented horizontally, for consistency and clarity of presentation, unless such interpretation would be inconsistent with the teachings of the present disclosure. The arrangements described in detail herein are illustrative and non-limiting examples; some disclosed elements can be oriented or ordered differently but within the scope of the present disclosure, to the extent that such variations are not illogical or non-functional, and are consistent with the teachings of the present disclosure in view of the art.

One object of some of the embodiments disclosed herein is to provide apparatus and methods for safe and expedient placement of an endotracheal tube into an airway of a patient.

Another object of some of the embodiments disclosed herein is to provide improved visualization of a patient's airway.

Still another object of some of the embodiments disclosed herein is to provide access to an airway of a patient that has difficult or unusual anatomy that would be difficult to access using prior art methods and devices.

Yet another object of some of the embodiments disclosed herein is to clear secretions, gastric contents, blood, or other unwanted material from the airway.

Exemplary claims include the following.

1. A laryngoscopic tracheoscope comprising: a laryngoscope member having a laryngoscope proximal portion and a laryngoscope distal portion, wherein the laryngoscope distal portion is configured to be inserted into a patient; the laryngoscope member including a first lumen extending between the laryngoscope proximal portion and the laryngoscope distal portion, the first lumen having a distal aperture at the laryngoscope distal portion, wherein the first lumen and distal aperture can accommodate a tracheoscope member and an endotracheal tube; a camera configured for imaging a portion of the airway of the patient; a suction system disposed proximate the camera to aid in clearing unwanted material which could otherwise obscure imaging from the camera.

2. The laryngoscopic tracheoscope of claim 1, further comprising: a tracheoscope member having a tracheoscope proximal portion and a tracheoscope distal portion; wherein the camera is a tracheoscope camera disposed on the tracheoscope distal portion and configured to view an interior portion of the body of the patient; a tracheoscope light disposed on the tracheoscope distal portion and configured to illuminate an interior portion of the body of the patient being viewed by the tracheoscope camera; wherein the suction system includes a distal tracheoscope suction aperture, wherein the distal tracheoscope suction aperture is arranged proximate at least one of the tracheoscope camera and the tracheoscope light; an endotracheal tube loaded onto the tracheoscope member, the endotracheal tube having an endotracheal tube distal portion; and wherein the first lumen has a distal aperture, and the tracheoscope distal portion and the endotracheal tube distal portion are configured to be advanced out of the first lumen through the distal aperture.

3. A laryngoscopic tracheoscope comprising: a laryngoscope member having a laryngoscope proximal portion and a laryngoscope distal portion, wherein the laryngoscope distal portion is configured to be inserted into a patient; a laryngoscope camera disposed on the laryngoscope distal portion and configured to view an interior portion of the body of the patient; a laryngoscope light disposed on the laryngoscope distal portion and configured to illuminate an interior portion of the body of the patient being viewed by the laryngoscope camera; and a suction system including a distal laryngoscope suction aperture, wherein the distal suction aperture is arranged proximate at least one of the laryngoscope camera and the laryngoscope light.

4. The laryngoscopic tracheoscope of claim 3, further comprising: a communication interface, wherein the communication interface is in communication with at least one of the laryngoscope camera, the laryngoscope light, and the suction system; and a graphical user interface configured to be coupled with the communication interface, wherein the graphical user interface includes at least one user selectable input for control of the laryngoscope camera, the laryngoscope light, and the suction system.

5. The laryngoscopic tracheoscope of claim 3, further comprising a first lumen extending between the laryngoscope proximal portion and the laryngoscope distal portion, the first lumen having a distal aperture at the laryngoscope distal portion, wherein the first lumen and distal aperture can accommodate a tracheoscope member and an endotracheal tube.

6. The laryngoscopic tracheoscope of claim 5, further comprising a tracheoscope member configured for passage within the first lumen.

7. The laryngoscopic tracheoscope of claim 5, wherein the first lumen includes a plurality of lumen segments.

8. The laryngoscopic tracheoscope of claim 7, further comprising a tracheoscope member configured for passage within the first lumen, and wherein when the tracheoscope is passed within the first lumen, the tracheoscope can be grasped at a location between two of the plurality of lumen segments in order to manipulate and position the tracheoscope.

9. The laryngoscopic tracheoscope of claim 5, further comprising: a tracheoscope member having a tracheoscope proximal portion and a tracheoscope distal portion, wherein the first lumen has a distal aperture, and the tracheoscope distal portion is configured to be advanced out through the distal aperture; a tracheoscope camera disposed on the tracheoscope distal portion and configured to view an interior portion of the body of the patient; a tracheoscope light disposed on the tracheoscope distal portion and configured to illuminate an interior portion of the body of the patient being viewed by the tracheoscope camera; and the suction system including a distal tracheoscope suction aperture, wherein the distal suction aperture is arranged proximate at least one of the tracheoscope camera and the tracheoscope light.

10. The laryngoscopic tracheoscope of claim 9, further comprising steering apparatus for flexing and straightening the tracheoscope distal portion, the steering apparatus including at least one pullwire.

11. The laryngoscopic tracheoscope of claim 10, wherein the steering apparatus includes a pullwire pulley.

12. The laryngoscopic tracheoscope of claim 9, further comprising a suction actuator for control of suction applied to clear unwanted material.

13. The laryngoscopic tracheoscope of claim 9, further comprising a deformable cover disposed at the laryngoscope proximal portion.

14. The laryngoscopic tracheoscope of claim 9, further comprising an endotracheal tube disposed about the tracheoscope member.

15. A laryngoscopic tracheoscope comprising: a laryngoscope member having a laryngoscope proximal portion and a laryngoscope distal portion, wherein the laryngoscope distal portion is configured to be inserted into a patient; a first lumen extending between the laryngoscope proximal portion and the laryngoscope distal portion, the first lumen having a distal aperture at the laryngoscope distal portion; a tracheoscope member having a tracheoscope proximal portion and a tracheoscope distal portion, wherein the tracheoscope distal portion is configured to be advanced out through the distal aperture; a camera apparatus selected from the group consisting of 1) a tracheoscope camera disposed at the tracheoscope distal portion, 2) a laryngoscope camera disposed at the laryngoscope distal portion, and 3) a tracheoscope camera disposed at the tracheoscope distal portion and a laryngoscope camera disposed at the laryngoscope distal portion; a light apparatus disposed to illuminate at least a portion of the patient viewed by the camera apparatus; and a suction system including a distal suction aperture, wherein the distal suction aperture is disposed proximate the camera apparatus to aid in clearing unwanted material which could otherwise obscure imaging from the camera apparatus.

16. The laryngoscopic tracheoscope of claim 15, wherein: the camera apparatus includes a tracheoscope camera disposed at the tracheoscope distal portion and a laryngoscope camera disposed at the laryngoscope distal portion; the light apparatus includes a tracheoscope light arranged to illuminate at least a portion of the patient viewed by the tracheoscope camera and a laryngoscope light arranged to illuminate at least a portion of the patient viewed by the laryngoscope camera; and the suction system including a distal suction aperture disposed proximate the tracheoscope camera to aid in clearing unwanted material which could otherwise obscure imaging from the tracheoscope camera, and a distal suction aperture disposed proximate the laryngoscope camera to aid in clearing unwanted material which could otherwise obscure imaging from the laryngoscope camera.

17. A method of placing an endotracheal tube in an airway of patient, the method comprising the steps of: providing a laryngoscopic tracheoscope including a laryngoscope member and a tracheoscope member and a suction system, the suction system including a laryngoscope distal suction aperture and a tracheoscope distal suction aperture; wherein the laryngoscope member includes a laryngoscope proximal portion and a laryngoscope distal portion, wherein the laryngoscope distal portion is configured to be inserted into a patient; wherein the laryngoscope member includes a first lumen extending between the laryngoscope proximal portion and the laryngoscope distal portion, the first lumen having a distal aperture at the laryngoscope distal portion; wherein the laryngoscope member includes a laryngoscope camera and a laryngoscope light and a laryngoscope distal suction aperture disposed at the laryngoscope distal portion; wherein the tracheoscope member includes a tracheoscope proximal portion and a tracheoscope distal portion, wherein the tracheoscope distal portion is configured to be advanced through the first lumen and out through the distal aperture; wherein the tracheoscope member includes a tracheoscope camera and a tracheoscope light and a tracheoscope distal suction aperture disposed at the tracheoscope distal portion; introducing the laryngoscope member into the airway of a patient and using the laryngoscope camera to facilitate positioning of the laryngoscope member; advancing the tracheoscope member through the first lumen and out through the distal aperture and using the tracheoscope camera to facilitate positioning of the tracheoscope member; actuating the suction system to draw unwanted material through the laryngoscope distal suction aperture and the tracheoscope distal suction aperture as desired; advancing an endotracheal tube over the tracheoscope member and position the endotracheal tube within the airway as desired; and removing the tracheoscope member and the laryngoscope member from the patient.

It is to be understood that even though numerous characteristics and advantages of the embodiments disclosed herein have been set forth in the foregoing description, together with details of the structure and function of the embodiments disclosed herein, the disclosure is illustrative only, and changes may be made in detail, especially in matters of shape, size, number, and arrangement of parts within the principles of the present disclosure to the full extent indicated by the broad general meaning of the terms in which the appended claims are expressed. Specific elements herein described with relation to any of the embodiments disclosed herein may be combined or substituted to the extent that such combination or substitution is consistent with the general functioning of the embodiments disclosed and the teachings herein, and as consistent with the appended claims.

What is claimed is:

1. A laryngoscopic tracheoscope comprising:
a laryngoscope member having a laryngoscope proximal portion and a laryngoscope distal portion, wherein the laryngoscope distal portion is configured to be inserted into a patient;
a laryngoscope camera disposed on the laryngoscope distal portion and configured to view an interior portion of the body of the patient;
a laryngoscope light disposed on the laryngoscope distal portion and configured to illuminate an interior portion of the body of the patient being viewed by the laryngoscope camera;
the laryngoscope member including a first lumen extending between the laryngoscope proximal portion and the laryngoscope distal portion, the first lumen having a distal aperture at the laryngoscope distal portion, wherein the first lumen and distal aperture can accommodate a tracheoscope member;
a suction system including a distal laryngoscope suction aperture, wherein the distal laryngoscope suction aperture is arranged proximate at least one of the laryngoscope camera and the laryngoscope light;
a tracheoscope member having a tracheoscope proximal portion and a tracheoscope distal portion, wherein the tracheoscope distal portion is configured to be advanced out through the distal aperture;
a tracheoscope camera disposed on the tracheoscope distal portion and configured to view an interior portion of the body of the patient;
a tracheoscope light disposed on the tracheoscope distal portion and configured to illuminate an interior portion of the body of the patient being viewed by the tracheoscope camera; and
the suction system including a distal tracheoscope suction aperture, wherein the distal suction aperture is arranged proximate at least one of the tracheoscope camera and the tracheoscope light.

2. The laryngoscopic tracheoscope of claim 1, further comprising:
a communication interface, wherein the communication interface is in communication with at least one of the laryngoscope camera, the laryngoscope light, and the suction system; and
a graphical user interface configured to be coupled with the communication interface, wherein the graphical user interface includes at least one user selectable input for control of the laryngoscope camera, the laryngoscope light, or the suction system.

3. The laryngoscopic tracheoscope of claim 1, wherein the first lumen and the distal aperture can accommodate an endotracheal tube.

4. The laryngoscopic tracheoscope of claim 3, wherein the first lumen includes a plurality of lumen segments.

5. The laryngoscopic tracheoscope of claim 4, wherein the tracheoscope member is configured for passage within the first lumen, and wherein when the tracheoscope member is passed within the first lumen, the tracheoscope member can be grasped at a location between two of the plurality of lumen segments in order to manipulate and position the tracheoscope member.

6. The laryngoscopic tracheoscope of claim 3, further comprising an endotracheal tube disposed about the tracheoscope member.

7. The laryngoscopic tracheoscope of claim 1, further comprising a steering apparatus for anteflexion and retroflexion and straightening the tracheoscope distal portion, the steering apparatus including at least one pullwire.

8. The laryngoscopic tracheoscope of claim 7, wherein the steering apparatus includes a pullwire pulley.

9. The laryngoscopic tracheoscope of claim 1, further comprising a suction actuator for control of suction applied to clear unwanted material.

10. The laryngoscopic tracheoscope of claim 1, further comprising a deformable cover disposed at the laryngoscope proximal portion to facilitate advancement through the larynx and into the trachea.

11. A laryngoscopic tracheoscope comprising:
a laryngoscope member having a laryngoscope proximal portion and a laryngoscope distal portion, wherein the laryngoscope distal portion is configured to be inserted into a patient;
a first lumen extending between the laryngoscope proximal portion and the laryngoscope distal portion, the first lumen having a distal aperture at the laryngoscope distal portion;
a tracheoscope member having a tracheoscope proximal portion and a tracheoscope distal portion, wherein the tracheoscope distal portion is configured to be advanced out through the distal aperture;

a camera apparatus including a tracheoscope camera disposed at the tracheoscope distal portion and a laryngoscope camera disposed at the laryngoscope distal portion;

a light apparatus including a tracheoscope light arranged to illuminate at least a portion of the patient viewed by the tracheoscope camera and a laryngoscope light arranged to illuminate at least a portion of the patient viewed by the laryngoscope camera; and a suction system including a tracheoscope distal suction aperture disposed proximate the tracheoscope camera to aid in clearing unwanted material which could otherwise obscure imaging from the tracheoscope camera, and a laryngoscope distal suction aperture disposed proximate the laryngoscope camera to aid in clearing unwanted material which could otherwise obscure imaging from the laryngoscope camera.

12. A method of placing an endotracheal tube in an airway of patient, the method comprising the steps of:

providing a laryngoscopic tracheoscope including a laryngoscope member and a tracheoscope member and a suction system, the suction system including a laryngoscope distal suction aperture and a tracheoscope distal suction aperture;

wherein the laryngoscope member includes a laryngoscope proximal portion and a laryngoscope distal portion, wherein the laryngoscope distal portion is configured to be inserted into a patient;

wherein the laryngoscope member includes a first lumen extending between the laryngoscope proximal portion and the laryngoscope distal portion, the first lumen having a distal aperture at the laryngoscope distal portion;

20 wherein the laryngoscope member includes a laryngoscope camera and a laryngoscope light and the laryngoscope distal suction aperture disposed at the laryngoscope distal portion;

wherein the tracheoscope member includes a tracheoscope proximal portion and a tracheoscope distal portion, wherein the tracheoscope distal portion is configured to be advanced through the first lumen and out through the distal aperture;

wherein the tracheoscope member includes a tracheoscope camera and a tracheoscope light and the tracheoscope distal suction aperture disposed at the tracheoscope distal portion;

introducing the laryngoscope member into the airway of a patient and using the laryngoscope camera to facilitate positioning of the laryngoscope member;

advancing the tracheoscope member through the first lumen and out through the distal aperture and using the tracheoscope camera to facilitate positioning of the tracheoscope member;

actuating the suction system to draw unwanted material through the laryngoscope distal suction aperture and the tracheoscope distal suction aperture as desired;

advancing an endotracheal tube over the tracheoscope member and positioning the endotracheal tube within the trachea, past the vocal cords, in the airway as desired; and removing the tracheoscope member and the laryngoscope member from the patient.

* * * * *